United States Patent
Wilkie et al.

(10) Patent No.: US 12,350,370 B2
(45) Date of Patent: *Jul. 8, 2025

(54) HUMIC AND FULVIC BLACK WATER BASED BEVERAGE FOR HUMAN CONSUMPTION

(71) Applicants: Louise Wilkie, Calabasas, CA (US); Jacqueline Wilkie, Calabasas, CA (US)

(72) Inventors: Louise Wilkie, Calabasas, CA (US); Jacqueline Wilkie, Calabasas, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/394,841

(22) Filed: Dec. 22, 2023

(65) Prior Publication Data

US 2024/0260615 A1  Aug. 8, 2024

Related U.S. Application Data

(63) Continuation of application No. 17/985,998, filed on Nov. 14, 2022, now Pat. No. 11,849,743, and a
(Continued)

(51) Int. Cl.
*A61K 9/12* (2006.01)
*A23B 2/05* (2025.01)
(Continued)

(52) U.S. Cl.
CPC ............. *A61K 9/1277* (2013.01); *A23B 2/05* (2025.01); *A23L 2/56* (2013.01); *A23L 2/68* (2013.01);
(Continued)

(58) Field of Classification Search
CPC ............ C02F 1/265; C02F 1/30; C02F 1/004; C02F 2103/08; C02F 2303/04; C02F 2101/14;
(Continued)

(56) References Cited

U.S. PATENT DOCUMENTS 2,380,800 A  *  7/1945  Smith .................. C02F 1/281
                                                          252/189
5,626,881 A  *  5/1997  Lown .................... A61K 35/10
                                                          514/960
(Continued)

FOREIGN PATENT DOCUMENTS

CN          1568827 A  *  1/2005
CN       104257843 A  *  1/2015
(Continued)

OTHER PUBLICATIONS

Full English Translation of Patent Publication CN-106497821A, published Mar. 2017. (Year: 2017).*
(Continued)

*Primary Examiner* — Joseph W Drodge
(74) *Attorney, Agent, or Firm* — Edmond DeFrank

(57) ABSTRACT

The embodiments disclose a method including processing and treating at least one water source supply for mixing with humic acid and fulvic acid, chopping and pulverizing at least one humate source, mixing the chopped and pulverized at least one humate source with the processed and treated at least one water source supply, processing the chopped and pulverized at least one humate source and the processed and treated at least one water source supply for separating, segregating, and suspending fulvic acid and humic acid molecules from the at least one humate source, storing the fulvic acid and humic acid molecules in a fresh quantity of the treated water source supply, adjusting the pH level of the stored fulvic acid and humic acid, and creating at least one or more beverage product for human consumption using the fulvic acid and humic acid molecule ingredients and other ingredients including vitamins, flavorings and additives.

14 Claims, 24 Drawing Sheets

Related U.S. Application Data continuation-in-part of application No. 17/962,461, filed on Oct. 7, 2022, said application No. 17/985,998 is a continuation of application No. 17/107,932, filed on Nov. 30, 2020, now Pat. No. 11,497,230, said application No. 17/962,461 is a continuation of application No. 16/594,039, filed on Oct. 6, 2019, now abandoned.

(51) Int. Cl.

| | | |
|---|---|---|
| *A23L 2/56* | (2006.01) | |
| *A23L 2/68* | (2006.01) | |
| *A23L 2/72* | (2006.01) | |
| *A23L 2/80* | (2006.01) | |
| *A23L 3/00* | (2006.01) | |
| *A61K 8/14* | (2006.01) | |
| *A61K 8/97* | (2017.01) | |
| *A61K 8/9794* | (2017.01) | |
| *A61K 9/08* | (2006.01) | |
| *A61K 9/1277* | (2025.01) | |
| *A61K 31/05* | (2006.01) | |
| *A61K 31/12* | (2006.01) | |
| *A61K 31/122* | (2006.01) | |
| *A61K 31/353* | (2006.01) | |
| *A61K 31/70* | (2006.01) | |
| *A61K 31/726* | (2006.01) | |
| *A61Q 19/08* | (2006.01) | |
| *C02F 1/00* | (2023.01) | |
| *C02F 1/28* | (2023.01) | |
| *C02F 1/32* | (2023.01) | |
| *C02F 1/66* | (2023.01) | |
| *C02F 1/68* | (2023.01) | |
| *C02F 101/12* | (2006.01) | |
| *C02F 103/32* | (2006.01) | |

(52) U.S. Cl.
CPC .............. *A23L 2/72* (2013.01); *A23L 2/80* (2013.01); *A61K 8/14* (2013.01); *A61K 8/9794* (2017.08); *A61K 9/08* (2013.01); *A61K 31/05* (2013.01); *A61K 31/122* (2013.01); *A61K 31/353* (2013.01); *A61K 31/726* (2013.01); *A61Q 19/08* (2013.01); *C02F 1/001* (2013.01); *C02F 1/283* (2013.01); *C02F 1/325* (2013.01); *C02F 1/66* (2013.01); *C02F 1/685* (2013.01); *C02F 1/686* (2013.01); *A23V 2002/00* (2013.01); *C02F 2101/12* (2013.01); *C02F 2103/32* (2013.01); *C02F 2303/04* (2013.01); *C02F 2303/16* (2013.01); *C02F 2303/185* (2013.01)

(58) Field of Classification Search
CPC .............. C02F 2209/06; C02F 2209/02; C02F 2103/26; C02F 2103/10; C02F 2103/007; C02F 1/008; C02F 1/02; C02F 1/32; C02F 1/68; C02F 1/685; C02F 1/686; C02F 1/78; C02F 9/00; C02F 2209/36; C02F 1/001; C02F 1/283; C02F 1/325; C02F 1/66; C02F 2101/12; C02F 2103/32; C02F 2303/16; C02F 2303/185; C02F 1/76; A23L 3/003; A23L 2/72; A23L 3/005; A23L 2/38; A23L 2/42; A23L 2/48; A23L 2/50; A23L 2/52; A23L 2/60; A23L 2/68; A23L 2/78; A23L 33/105; A23L 3/00; A23L 3/001; A23L 3/3409; A23L 3/3418; A23L 2/56; A23L 2/80; A23L 3/28; B67C 7/0073; B67C 3/007; B67C 3/0073; B67C 2003/228; A61K 33/00; A61K 9/0031; A61K 9/0095; A61K 9/02; A61K 9/025; A61K 9/08; A61K 31/185; A61K 31/19; A61K 36/00; A61K 36/899; A61K 9/1277; A61K 8/14; A61K 8/9794; A61K 31/05; A61K 31/122; A61K 31/353; A61K 31/726; A61K 9/0014; A61K 9/0056; A61K 9/006; A61K 9/127; A61K 36/185; A61K 36/886; C12G 3/04; C12G 3/08; C12G 3/085; C12C 12/00; C12C 12/002; A61L 2/0017; A61L 2/0023; A61L 2/0047; A61L 2/02; A61L 2/022; A61L 2/04; A61L 2/08; A61L 2/10; A61L 2/28; A23V 2002/00; G16B 50/30; G06Q 50/02; B01D 1/00; B01D 5/00; B01D 11/0207; B01D 11/028; B01D 29/00; B01D 29/0047; B01D 29/0052; B01D 29/0059; B01D 29/60; B01D 36/00; B01D 36/02; A61Q 19/08; A61Q 7/00; A61Q 11/00; A61Q 19/00
USPC ......... 210/85, 134, 143, 149, 175, 192, 335, 210/739, 764, 767, 774; 159/47.1; 426/388, 390, 392, 394, 419, 478, 479, 426/481, 514, 519, 590, 592, 615; 424/408, 422, 436, 725, 630, 641; 366/154.1, 162.1, 177.1, 197, 204; 99/275, 286, 287, 290, 537, 623; 604/285, 288; 206/528, 529; 514/966
See application file for complete search history.

(56) References Cited

U.S. PATENT DOCUMENTS

| | | | | |
|---|---|---|---|---|
| 10,421,670 | B1* | 9/2019 | Wilkie | C02F 1/30 |
| 10,849,340 | B2* | 12/2020 | Wilkie | A23L 3/005 |
| 10,894,937 | B2* | 1/2021 | Wilkie | A23L 2/58 |
| 10,918,690 | B2* | 2/2021 | Wilkie | G06Q 50/02 |
| 10,934,511 | B2* | 3/2021 | Wilkie | B67C 7/0073 |
| 11,497,230 | B2* | 11/2022 | Wilkie | C02F 1/68 |
| 11,849,743 | B2* | 12/2023 | Wilkie | A23L 3/005 |
| 2003/0150796 | A1* | 8/2003 | Heinig, Jr. | C02F 1/505 |
| | | | | 210/502.1 |
| 2007/0154614 | A1* | 7/2007 | Sherwood | A23L 3/0155 |
| | | | | 426/583 |
| 2008/0311253 | A1* | 12/2008 | Mower | A23L 33/16 |
| | | | | 426/72 |
| 2012/0152755 | A1* | 6/2012 | Martin | A61K 33/00 |
| | | | | 205/335 |
| 2012/0183657 | A1* | 7/2012 | Marina | B65D 81/3222 |
| | | | | 215/6 |
| 2012/0207850 | A1* | 8/2012 | Martin | A61K 9/0009 |
| | | | | 514/724 |
| 2012/0213756 | A1* | 8/2012 | Petralia | A61K 36/886 |
| | | | | 424/94.1 |
| 2014/0010922 | A1* | 1/2014 | Martin | A23L 2/38 |
| | | | | 426/66 |
| 2015/0329225 | A1* | 11/2015 | Moncayo, Jr. | A61L 2/07 |
| | | | | 422/26 |
| 2015/0344399 | A1* | 12/2015 | Martin | C10L 1/023 |
| | | | | 562/488 |
| 2016/0008417 | A1* | 1/2016 | Vandecar | A61K 36/48 |
| | | | | 424/549 |
| 2016/0095877 | A1* | 4/2016 | Martin | A23L 2/52 |
| | | | | 514/724 |
| 2017/0129820 | A1* | 5/2017 | Li | C05D 1/00 |

(56) References Cited

U.S. PATENT DOCUMENTS

2018/0028473 A1\* 2/2018 Pomytkin .............. A61K 33/00
2018/0193403 A1\* 7/2018 George .................. A61P 35/00

FOREIGN PATENT DOCUMENTS

| CN | 106497821 A | \* | 3/2017 | ........... A61K 9/0095 |
| CN | 107260842 A | \* | 10/2017 | ......... A23V 2002/00 |
| KR | 100549662 B1 | \* | 2/2006 | .............. A41B 9/02 |
| TR | 201704453 A2 | \* | 4/2018 | |

OTHER PUBLICATIONS

Full English Translation of Patent Publication CN-107260842A, published Oct. 2017. (Year: 2017).\*
Full English Translation of Murat Sevinc publication TR201704453A2, published Apr. 2018. (Year: 2018).\*
Full English Translation of Patent Publication CN-104257843A, published Jan. 2015. (Year: 2015).\*
EnglishTranslation of Patent Publication KR 100549662B1, published Feb. 7, 2006. (Year: 2006).\*
English Translation of Patent Publication CN 1568827-A, published Jan. 26, 2005. (Year: 2005).\*

\* cited by examiner

HUMIC AND FULVIC BLACK WATER BASED BEVERAGE FOR HUMAN CONSUMPTION

This patent application is a Continuation of and claims priority to U.S. patent application entitled: "HUMIC AND FULVIC MINERAL EXTRACTION METHOD AND BEVERAGE FOR HUMAN CONSUMPTION", U.S. Ser. No. 17/985,998, filed on Nov. 14, 2022 by Louise Wilkie, which is a Continuation of and claims priority to U.S. patent application entitled: "HUMIC AND FULVIC MINERAL EXTRACTION METHOD AND BEVERAGE FOR HUMAN CONSUMPTION", U.S. Ser. No. 17/107,932, filed on Nov. 30, 2020, which is a Continuation of and claims priority to U.S. patent application entitled: "HUMIC AND FULVIC MINERAL EXTRACTION METHOD AND BEVERAGE FOR HUMAN CONSUMPTION", U.S. Ser. No. 16/030,962, filed on Jul. 10, 2018, this patent application is also a Continuation-in part of and claims priority to U.S. patent application entitled: "METHOD AND DEVICES FOR CELLULAR TRANSFER OF COMPOUNDS WITH AUGMENTED REALITY APPLICATION", U.S. Ser. No. 17/962,461 filed on Oct. 7, 2022, which is a Continuation of and claims priority to U.S. patent application entitled: "METHOD AND DEVICES FOR CELLULAR TRANSFER OF COMPOUNDS WITH AUGMENTED REALITY APPLICATION", U.S. Ser. No. 16/594,039, filed on Oct. 6, 2019, this patent application is also a Continuation-in part of and claims priority to U.S. patent application entitled: "NUTRITIONAL SUPPLEMENT BLACK SHOT MIXTURE METHOD AND APPARATUS", U.S. Ser. No. 17/940,926 filed on Sep. 8, 2022, which is a Continuation of and claims priority to U.S. patent application entitled: "CARBON HOOKS COMPOUND BONDING METHOD AND APPARATUS", U.S. Ser. No. 16/751,447 filed on Jan. 24, 2020, this patent application is also a Continuation-in part of and claims priority to U.S. patent application entitled: "FULVIC ACID AND HUMIC ACID NUTRACEUTICAL SUPPLEMENT SHOT AND METHOD", U.S. Ser. No. 17/151,658 filed on Jan. 18, 2021, which is a Continuation of and claims priority to U.S. patent application entitled: "HUMIC AND FULVIC MINERAL EXTRACTION METHOD AND BEVERAGE FOR HUMAN CONSUMPTION" U.S. Ser. No. 16/751,562, filed on Jan. 24, 2020, wherein all the above U.S. patent applications are incorporated herein by reference.

BACKGROUND

Humic and fulvic acids are extracted using a number of chemical processes that add chemicals which are not suitable for human consumption. Those extracted humus sourced acids are used in fertilizers for agricultural use and in some cases added to animal feeds. Some of the chemicals used in the processes and some of the processes introduce chemicals borne in water that can produce chemical reactions or leave residual amounts that are known carcinogens. An extraction method to extract both humic and fulvic acids for human consumption should not include the use of those or similar types of chemicals and eliminate any added chemicals that could be present in any mixing water.

DETAILED DESCRIPTION OF THE INVENTION

In a following description, reference is made to the accompanying drawings, which form a part hereof, and in which is shown by way of illustration a specific example in which the invention may be practiced. It is to be understood that other embodiments may be utilized and structural changes may be made without departing from the scope of the embodiments.

General Overview

It should be noted that the descriptions that follow, for example, in terms of a black water beverage method and devices is described for illustrative purposes and the underlying system can apply to any number and multiple types of apparatuses and processes. In one embodiment of the present invention, the black water beverage method and devices can be configured using at least one or more humate sources to extract humic and fulvic acids of one embodiment. The black water beverage method and devices can be configured to include at least one or more beverage product and can be configured to include black water, soft drinks and alcoholic beverages using the embodiments.

Figure 1:
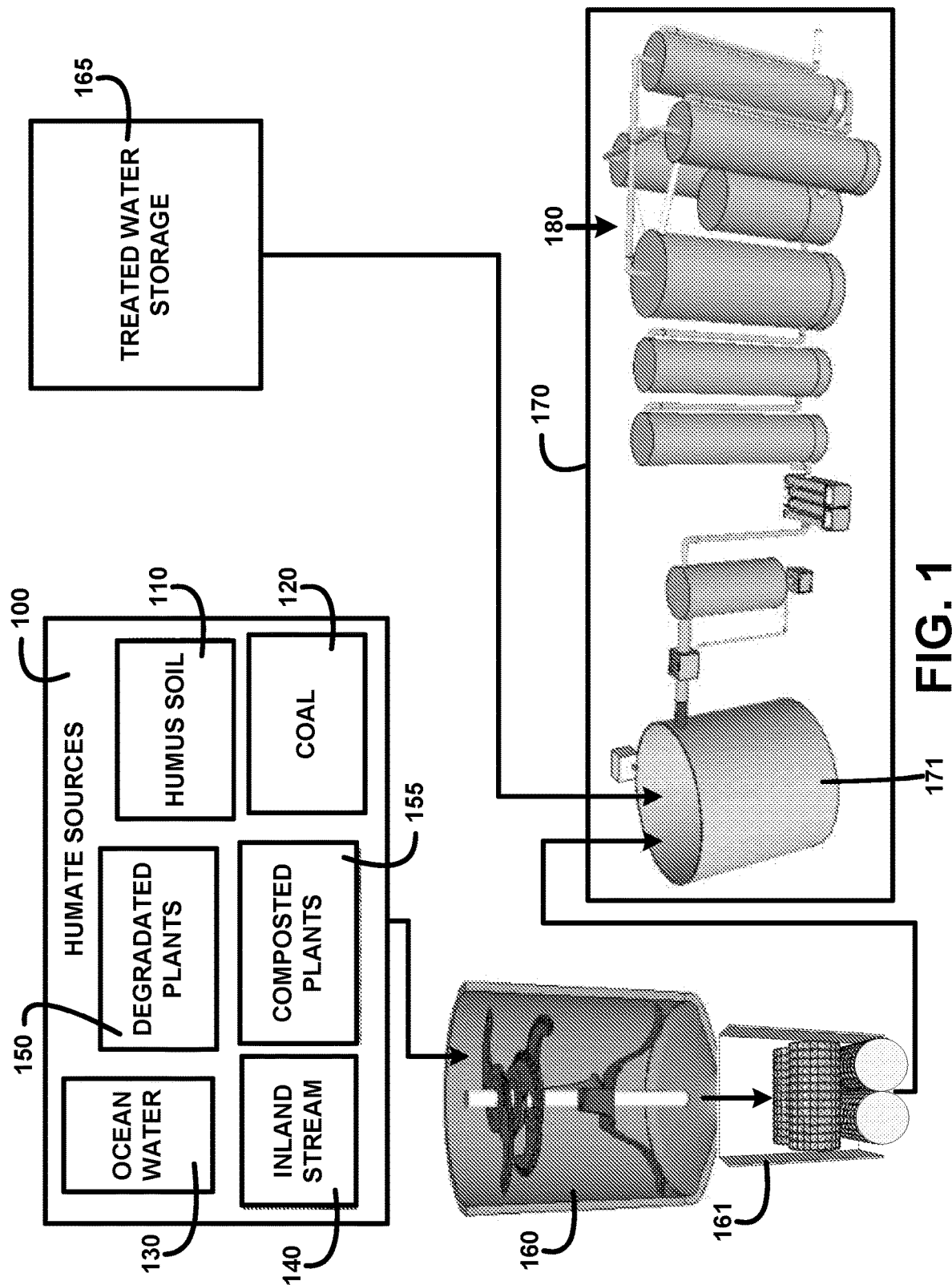
FIG. 1 shows a block diagram of an overview of black water humic and fulvic acids extraction for human consumption method and devices of one embodiment.

FIG. 1 shows a block diagram of an overview of black water humic and fulvic acids extraction for human consumption method and devices of one embodiment. FIG. 1 shows humate sources 100 including humus soil 110, coal 120, ocean water 130, inland stream 140 and degradated plants 150. Treated water storage 165 contains a water source purified with various processes that produce potable water. The treated water is mixed with at least one of the humate sources 100 that have been processed using a humate materials chopper 160 and chopped humate materials pulverizer 161 in a mixing tank 171. The humate and treated water mixture filtration, dechlorination, defluoridation, sterilization, pH adjustment and temperature control devices and processes 170 is followed by humic and fulvic acid molecules separation and segregated storage suspended in purified water 180. The black water humic and fulvic acids extraction for human consumption method and devices processes and devices are controlled using digital processors, digital servers, digital computers, digital sensors, digital analyzers, digital valves, digital pumps, and other digitally controlled devices including wireless digital devices for automating individual process steps and operations. These processes produce humic and fulvic acids that are suitable for human consumption in for example a water beverage, flavored beverages, alcoholic beverages, supplements and food additives of one embodiment.

DETAILED DESCRIPTION

Figure 2:
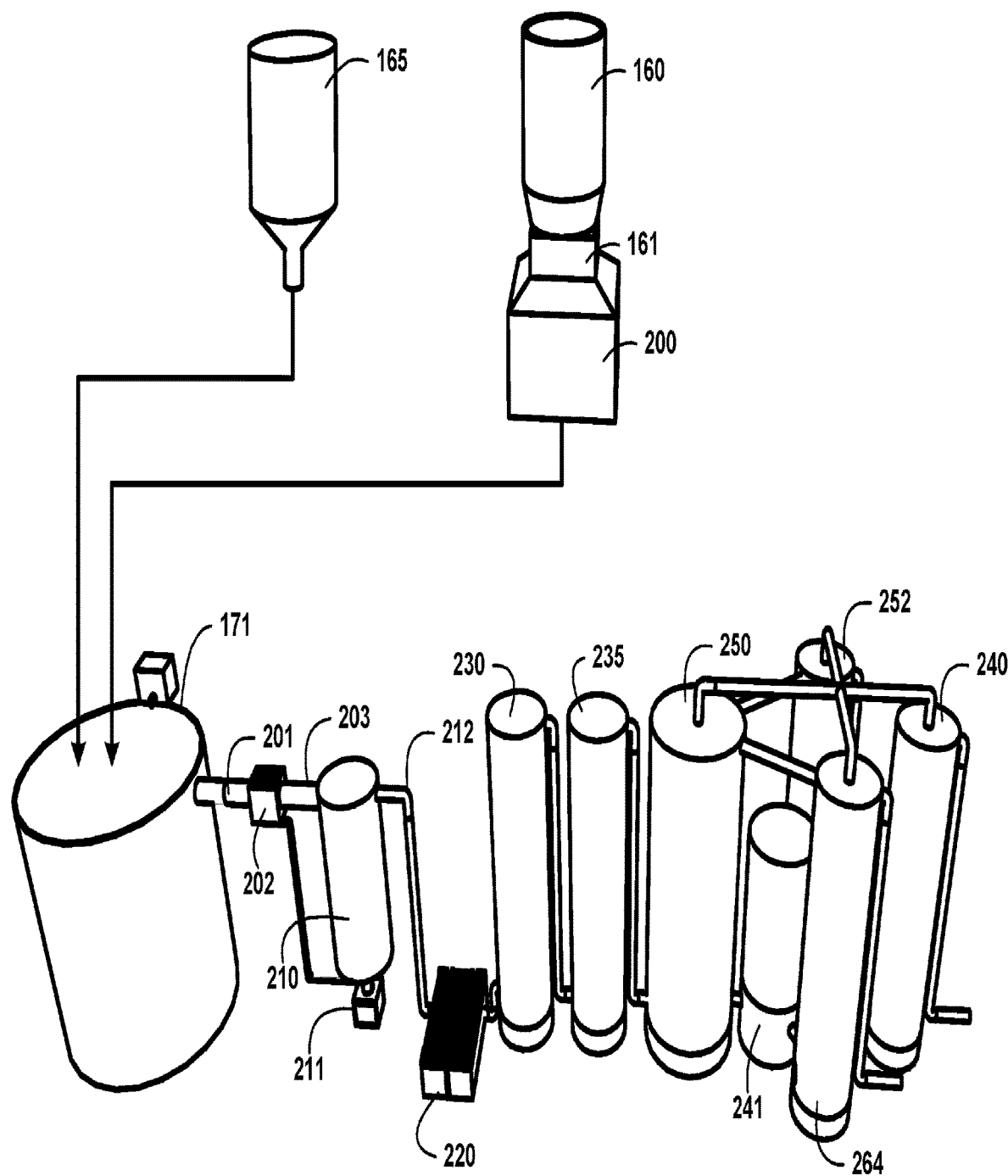
FIG. 2 shows for illustrative purposes only an example of black water humic and fulvic acids extraction for human consumption method and devices of one embodiment.

FIG. 2 shows for illustrative purposes only an example of black water humic and fulvic acids extraction for human consumption method and devices of one embodiment. FIG. 2 shows a process wherein at least one of the humate sources 100 of FIG. 1 is processed in the humate materials chopper 160 and chopped humate materials pulverizer 161 then collected in a chopped-pulverized humate material storage 200 and deposited in the mixing tank 171 with a quantity of treated water from the treated water storage 165. A humate-treated water mixture supply piping 201 conveys the mixture to a first stage raw water particulate filtration 202. A filtered humate-treated water mixture supply 203 is processed through a second stage humate-treated water mixture particulate filtration settling tank 210. The particulates filtered out of the mixture are accumulated in a particulate disposal container 211 of one embodiment.

UV light dechlorination 220 is performed on the mixture before it is processed to an adsorption defluoridation device 230 with granular activated carbon (GAC). The fluoride molecules adsorb to surfaces of the granular activated carbon (GAC). A fresh treated water storage tank 240 with a fresh treated water temperature control device and a pH control device 241 is used to supply additional water and control the desired PH level. The pH level is regulated to be greater than or equal than 8.5 and less than 10. A fresh treated water supply pipe 242 is used to convey treated water to a humic-fulvic acid separation chamber 250 with a bed of activated carbon material, a separation vacuum device, temperature regulating device and pH control device 241. The fulvic acid separation vacuum device and temperature regulating device process the separated fulvic acid molecules that have concentrated in the humic-fulvic acid separation chamber 250. The separation vacuum device uses a vacuum pressure to draw the concentrated fulvic acid molecules into a fulvic acid storage tank 252 with temperature and pH control device 241 of one embodiment.

A first humic acid separation chamber 260 with a humic acid separation vacuum device and temperature regulating device 263 in a second humic acid separation chamber 261 is used to draw separated humic acid molecules that have concentrated in the second humic acid separation chamber 262 into a humic acid storage tank 264 with temperature and pH control device 241. The segregated fulvic and humic acid molecules suspended in the treated water are stored for use in products of one embodiment.

Figure 3A:
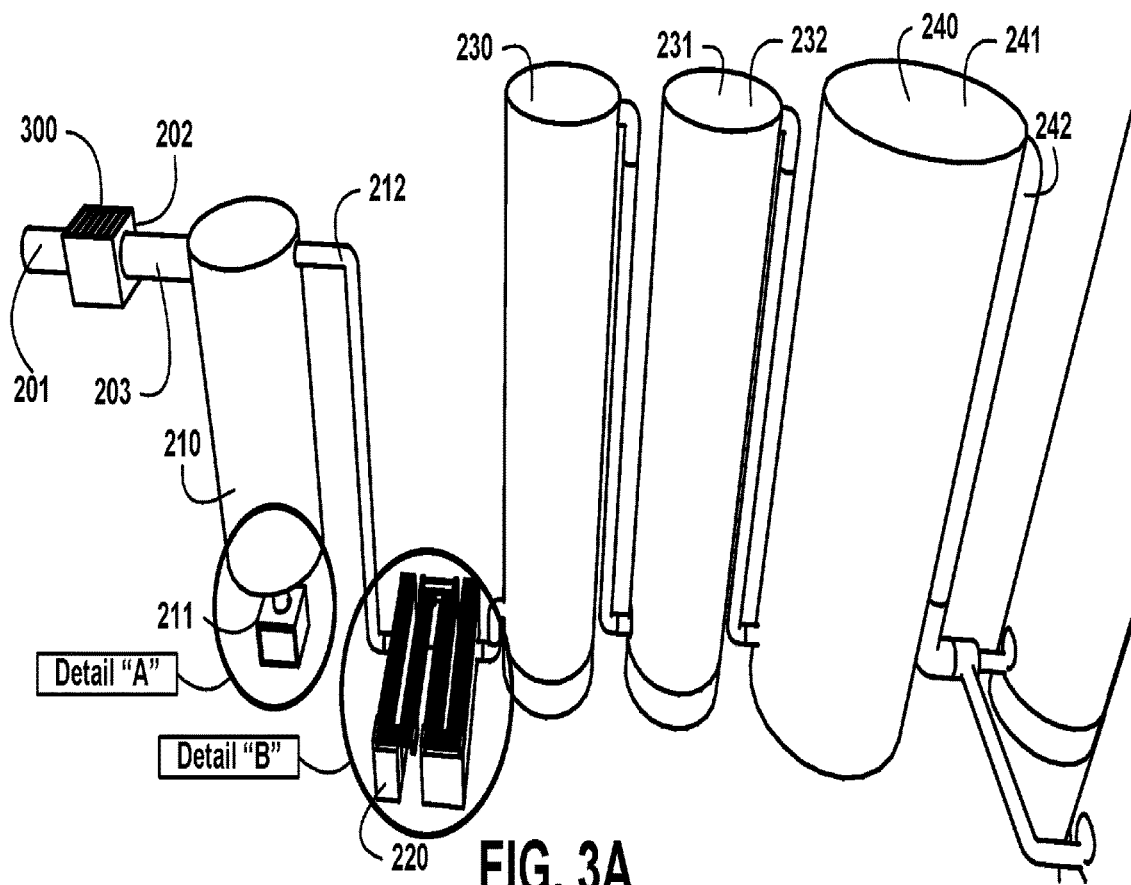
FIG. 3A shows for illustrative purposes only an example humic and fulvic acids extraction and separation of one embodiment.

Humic and Fulvic Acids Extraction and Separation:

FIG. 3A shows for illustrative purposes only an example of humic and fulvic acids extraction and separation of one embodiment. FIG. 3A shows the humate-treated water mixture supply piping 201 conveying the mixture to the first stage humate-treated water mixture particulate filtration 202. The humate-treated water mixture particulate filtration process 202 includes removable filter elements 300. The filtered humate-treated water mixture supply 203 is processed through the second stage humate-treated water mixture particulate filtration settling tank 210. Particulates filtered out of the mixture are conveyed to the particulate waste disposal container 211 and second stage particulate disposal container 212 of one embodiment.

The UV light dechlorination 220 process is followed by conveying the mixture to the adsorption defluoridation device 230. Chlorine and fluoride are found in water and can be found in humate sources through run-off of municipal water used domestically and by irrigation. These can be harmful to humans at differing concentrations. After defluoridation settled ha-fa suspended mixture is stored in a settled ha-fa suspended mixture storage tank 235. Supplemental water during the process is supplied from the fresh treated water storage tank 240 with the fresh treated water temperature control device through the fresh treated water supply pipe of one embodiment.

Figure 3B:
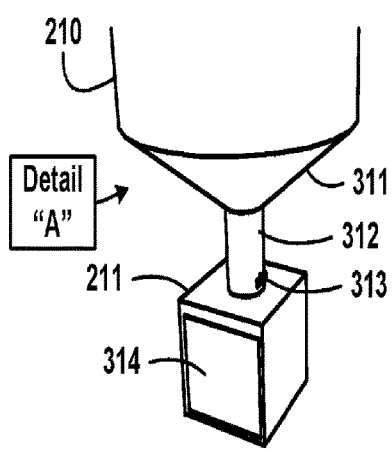
FIG. 3B shows for illustrative purposes only an example humic and fulvic acids extraction particulate waste separation of one embodiment.

Humic and Fulvic Acids Extraction Particulate Waste Separation:

FIG. 3B shows for illustrative purposes only an example of humic and fulvic acids extraction particulate waste separation of one embodiment. FIG. 3B shows a particulate waste accumulator funnel 311 used to accumulate the particulate waste at the particulate waste disposal discharge pipe 312 that includes a butterfly valve 313. The butterfly valve 313 is opened to pass the particulate waste to the particulate waste disposal container 211. The particulate waste disposal container 211 includes a particulate waste water dehydrator 314 to dry the particulate waste for dry disposal and wet disposal of any liquid residue of one embodiment.

Figure 3C:
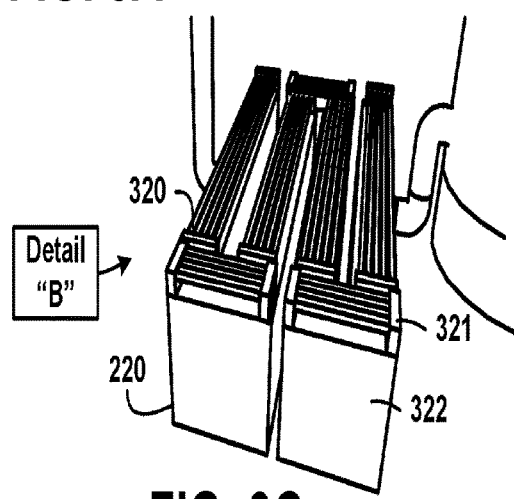
FIG. 3C shows for illustrative purposes only an example humic and fulvic acids extraction sterilization of one embodiment.

Humic and Fulvic Acids Extraction Sterilization:

FIG. 3C shows for illustrative purposes only an example of humic and fulvic acids extraction sterilization of one embodiment. FIG. 3C shows the UV light dechlorination 220 processor that includes UV light high intensity bulbs 320 and UV light ballast 321. The high intensity wave length UV light beams pass through the aqueous mixtures as it flows through a filtered humate-treated water mixture supply serpentine channel 322. The serpentine channel 322 is fabricated to allow a predetermined amount of UV light exposure to the aqueous mixture to kill microorganisms of one embodiment.

Figure 4:
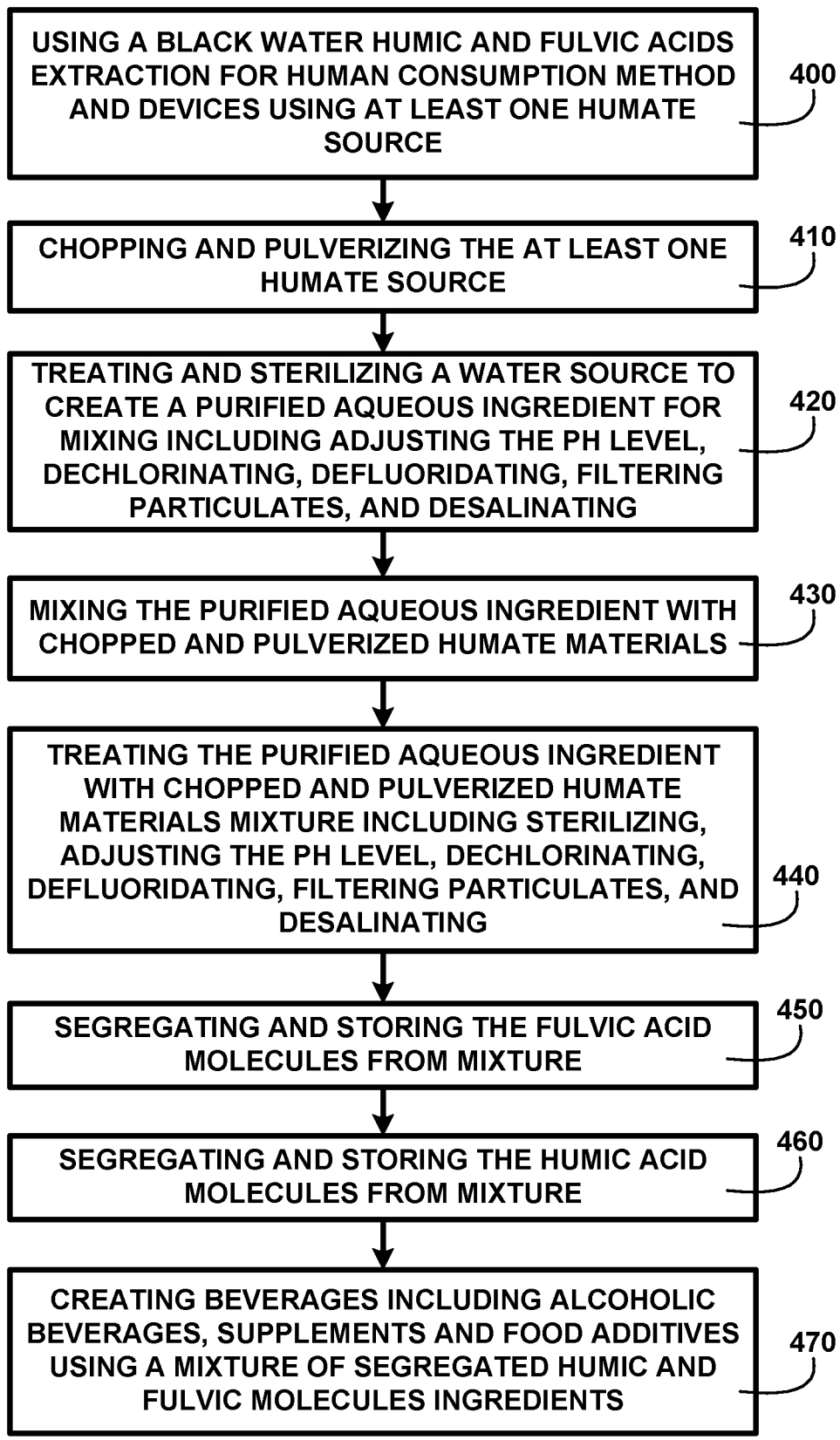
FIG. 4 shows for illustrative purposes only an example of extraction for human consumption processing of one embodiment.

Extraction for Human Consumption Processing:

FIG. 4 shows for illustrative purposes only an example of extraction for human consumption processing of one embodiment. FIG. 4 shows using black water humic and fulvic acids extraction for human consumption method and devices using at least one humate source 400. A process is used for chopping and pulverizing the at least one humate source 410. Processing includes treating and sterilizing a water source to create a purified aqueous ingredient for mixing including adjusting the pH level, dechlorinating, defluoridating, filtering particulates, and desalinating 420. The processed humate source and treated and sterilized water are deposited into a mixing tank for mixing the purified aqueous ingredient with chopped and pulverized humate materials 430. The mixture ingredients are processed by treating the purified aqueous ingredient with chopped and pulverized humate materials mixture including sterilizing, adjusting the pH level, dechlorinating, defluoridating, filtering particulates, and desalinating 440. Processing continues for segregating and storing the fulvic acid molecules from mixture 450 and segregating and storing the humic acid molecules from mixture 460. The humic and fulvic acids extracted, segregated and suspended in an aqueous solution are used for creating water beverage, flavored beverages, alcoholic beverages, supplements and food additives using a mixture of segregated humic and fulvic molecules ingredients 470 of one embodiment.

Figure 5:
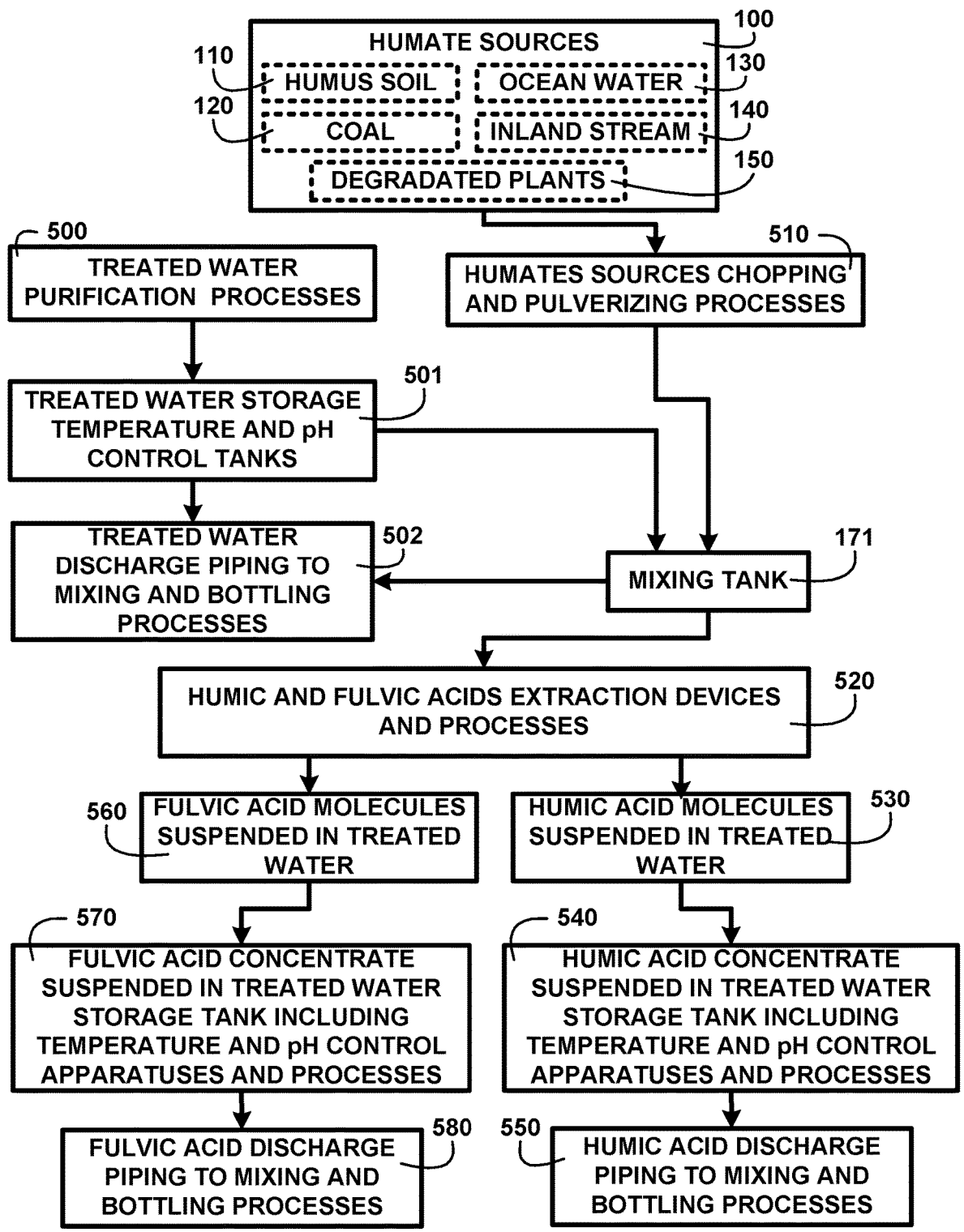
FIG. 5 shows for illustrative purposes only an example of humic and fulvic acids extraction devices and processes of one embodiment.

Humic and Fulvic Acids Extraction Devices and Processes:

FIG. 5 shows for illustrative purposes only an example of humic and fulvic acids extraction devices and processes of one embodiment. FIG. 5 shows humate sources 100 including humus soil 110, coal 120, ocean water 130, inland stream water 140, and degradated plants 150. Treated water purification processes 500 are used to create potable water for human consumption and is stored in treated water storage temperature and pH control tanks 501. The treated water processes 500 can include creating oxygenated water using electrolysis and distilled water for human consumption. Treated water discharge piping to mixing and bottling processes 502 is used to deposit treated water to the mixing tank 171. Humates sources chopping and pulverizing processes 510 prepare the humate sources for deposition into the mixing tank 171 with the treated water. Humic and fulvic acids extraction devices and processes 520 are used to separate humic acid molecules suspended in treated water 530 which are stored in humic acid concentrate suspended in treated water storage tank including temperature and pH control apparatuses and processes 540. The processed humic acid concentrate is conveyed through a humic acid discharge piping to mixing and bottling processes 550. Fulvic acid molecules suspended in treated water 560 are stored in fulvic acid concentrate suspended in treated water storage tank including temperature and pH control apparatuses and processes 570. The processed fulvic acid concentrate is conveyed through fulvic acid discharge piping to mixing and bottling processes 580 of one embodiment.

Figure 6:
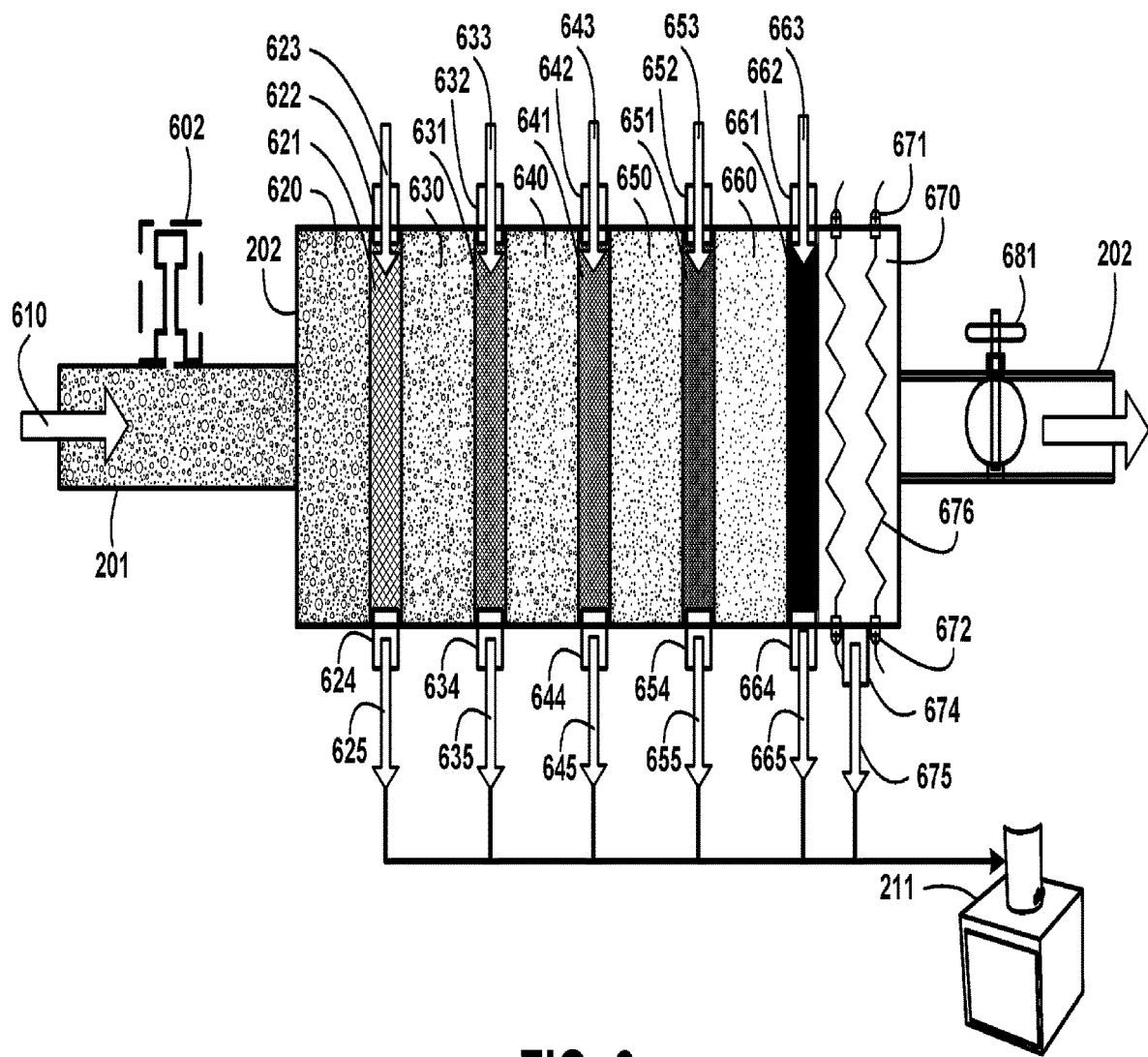
FIG. 6 shows for illustrative purposes only an example of first stage humate-treated water mixture particulate filtration of one embodiment.

First Stage Humate-Treated Water Mixture Particulate Filtration:

FIG. 6 shows for illustrative purposes only an example of first stage humate-treated water mixture particulate filtration of one embodiment. FIG. 6 shows the humate-treated water mixture supply piping 201 conveying a humate-treated water mixture supply 610 to a process. The humate-treated water mixture supply 610 is processed using pH sensors and PH level adjustment devices 602 to adjust the pH to a desired level. The pH level is adjusted to maintain a pH in which humic acid molecules are soluble in water. The first stage humate-treated water mixture particulate filtration 202 conveys an unfiltered humate-treated water mixture 620 through a first stage particulate filter 621. The first stage particulate filter 621 is a mesh at a predetermined size to block particulates of a size greater than the mesh openings. A first stage particulate filter treated water flush supply pipe 622 supplies first stage particulate filter flush treated water 623 to flush the blocked particulates off of the first stage particulate filter 621 to prevent clogging of mesh openings and allow the remaining fluid to pass through. The first stage particulate filter flush treated water 623 exits the first stage particulate filter 621 through a first stage particulate filter treated water flush discharge pipe 624 and first stage particulate filter flush treated water discharge 625 is conveyed to the particulate disposal container 211 of one embodiment.

A first stage particulate filtered humate-treated water mixture 630 is passed through a second stage particulate filter 631 mesh at a predetermined size to block particulates of a size greater than the mesh openings. A second stage particulate filter treated water flush supply pipe 632 conveys second stage particulate filter flush treated water 633 to clean the second stage particulate filter 631. The flush water exits through a second stage particulate filter treated water flush discharge pipe 634 wherein second stage particulate filter flush treated water discharge 635 is conveyed to the particulate disposal container 211 of one embodiment.

A second stage particulate filtered humate-treated water mixture 640 is passed through a third stage particulate filter 641 with a predetermined sized mesh to block particulates of a size greater than the mesh openings. A third stage particulate filter treated water flush supply pipe 642 conveys third stage particulate filter flush treated water 643 used to flush blocked particulates off of the third stage particulate filter 641. A third stage particulate filter treated water flush discharge pipe 644 conveys third stage particulate filter flush treated water discharge 645 to the particulate disposal container 211 of one embodiment.

A third stage particulate filtered humate-treated water mixture 650 passes through a fourth stage particulate filter 651 with a particulate blocking mesh of a predetermined size to block particulates larger than the mesh openings. Fourth stage particulate filter flush treated water 653 passes through a fourth stage particulate filter treated water flush supply pipe 652 to clean the fourth stage particulate filter 651. A fourth stage particulate filter treated water flush discharge pipe 654 passes fourth stage particulate filter flush treated water discharge 655 to the particulate disposal container 211 of one embodiment.

A fourth stage particulate filtered humate-treated water mixture 660 flows through a fifth stage particulate filter 661 with a mesh of a predetermined size to block particulates larger than the predetermined size. A fifth stage particulate filter treated water flush supply pipe 662 supplies fifth stage particulate filter flush treated water 663 to clean the fifth stage particulate filter 661 of blocked particulate which pass out of the filter through a fifth stage particulate filter treated water flush discharge pipe 664. Fifth stage particulate filter flush treated water discharge 665 is conveyed to the particulate disposal container 211. The fifth stage particulate filtered humate-treated water mixture 670 passes through piping to the next processes of one embodiment.

Figure 7:
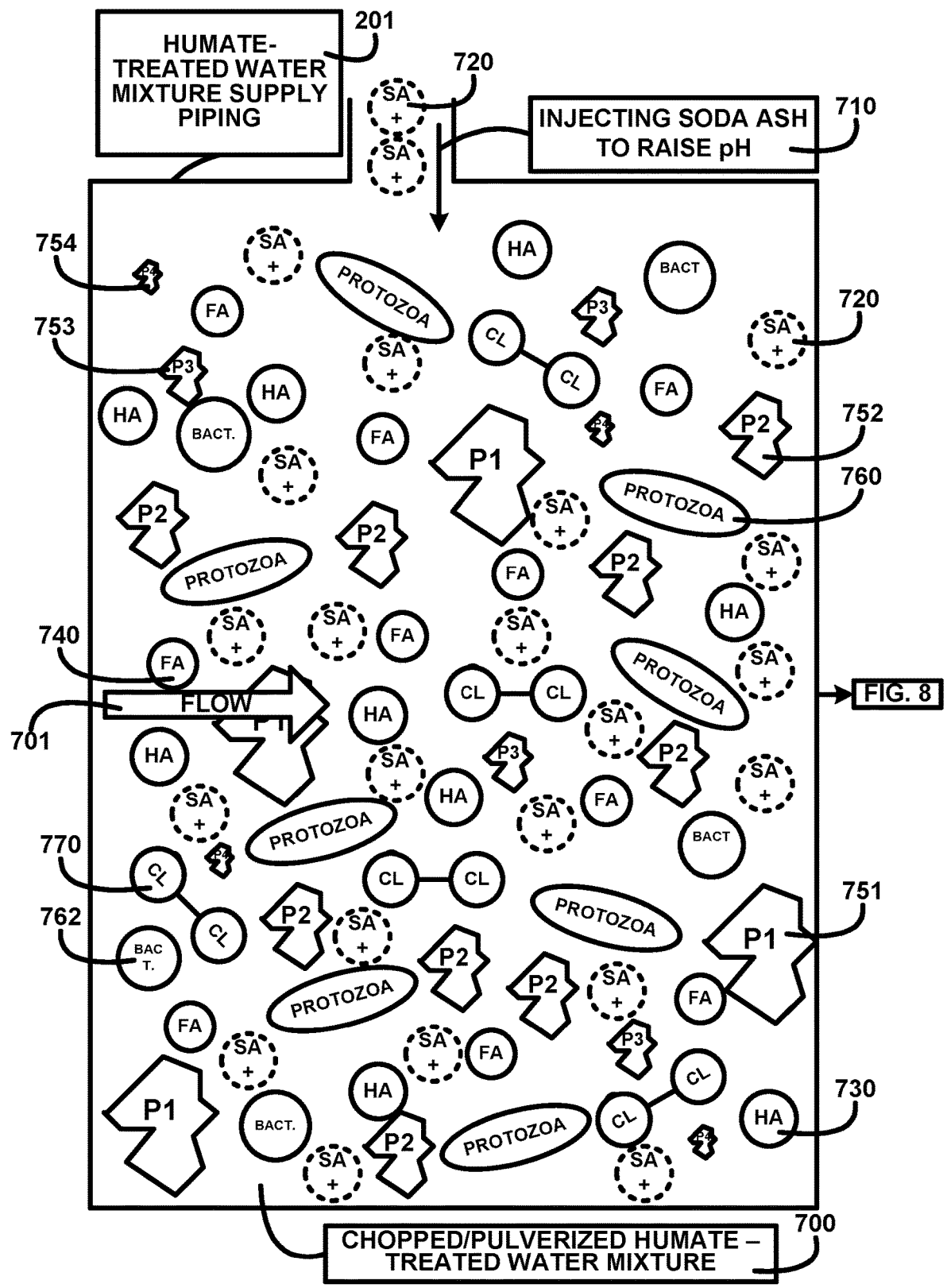
FIG. 7 shows for illustrative purposes only an example of chopped/pulverized humate-treated water mixture constituents of one embodiment.

Chopped/Pulverized Humate-Treated Water Mixture Constituents:

FIG. 7 shows for illustrative purposes only an example of chopped/pulverized humate-treated water mixture constituents of one embodiment. FIG. 7 shows chopped/pulverized humate-treated water mixture constituents 700 in the humate-treated water mixture supply piping 201. The mixture flow 701 is treated by injecting soda ash to raise pH 710 above the pH level of humic acid solubility. The chopped/pulverized humate-treated water mixture constituents 700 include s+ soda ash molecule 720, p2 particulate size 2 752, protozoa microorganism 760, p1 particulate size 1 751, p3 particulate size 3 753, p4 particulate size 4 754, ha humic acid molecule 730, bact. bacteria microorganism 762, cl chlorine molecule 770, fa fulvic acid molecule 740 of one embodiment. Descriptions of further processing are shown in FIG. 8.

Figure 8:
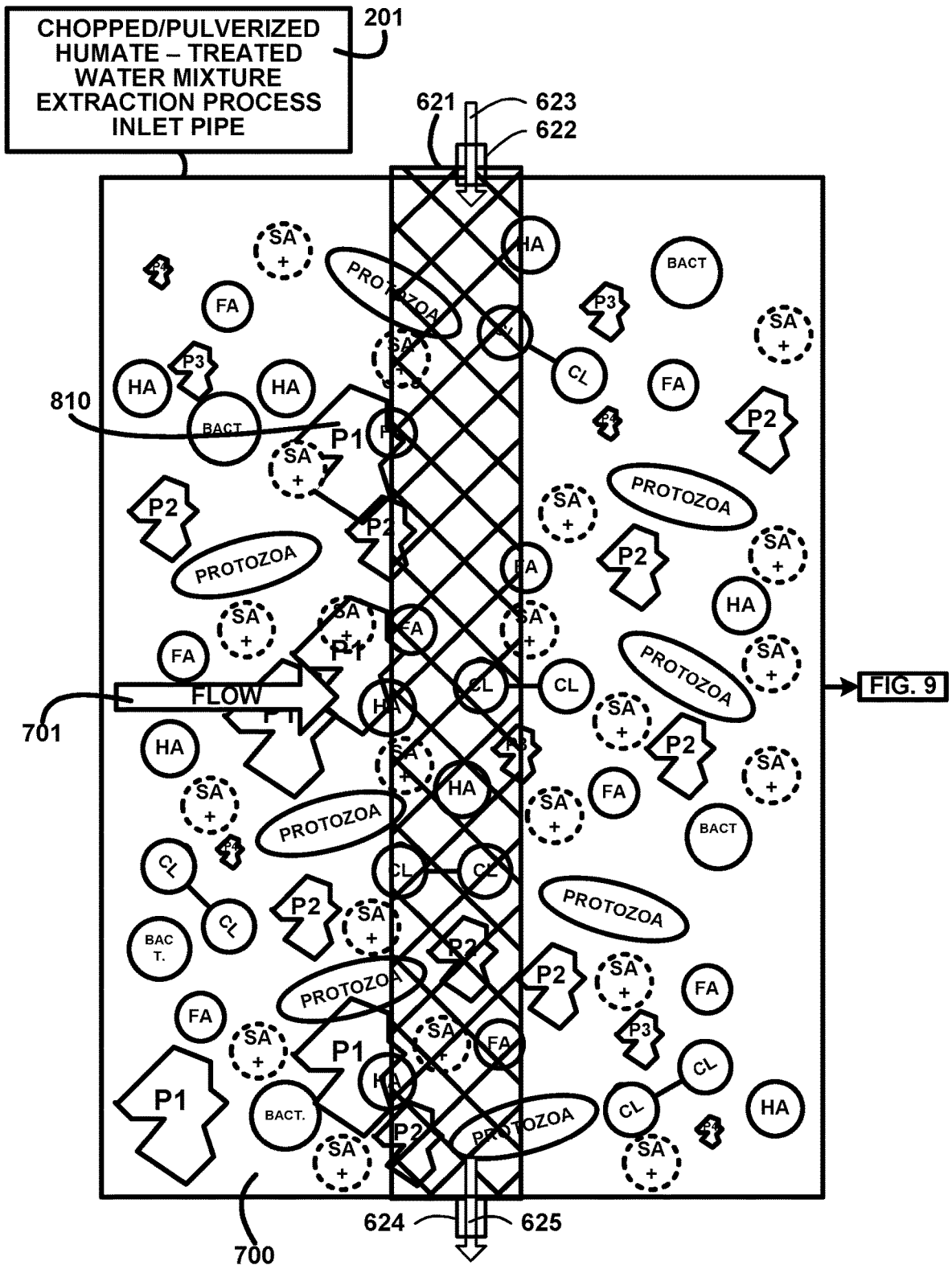
FIG. 8 shows for illustrative purposes only an example of first stage particulate filter of one embodiment.

First Stage Particulate Filter:

FIG. 8 shows for illustrative purposes only an example of first stage particulate filter of one embodiment. FIG. 8 shows continuing from FIG. 7 the humate-treated water mixture supply piping 201 conveys the mixture to the first stage particulate filter 621 flow 701 where p1 particulate size 1 are blocked 810 from the chopped/pulverized humate-treated water mixture 700 of one embodiment. The description of the process continues on FIG. 9.

Figure 9:
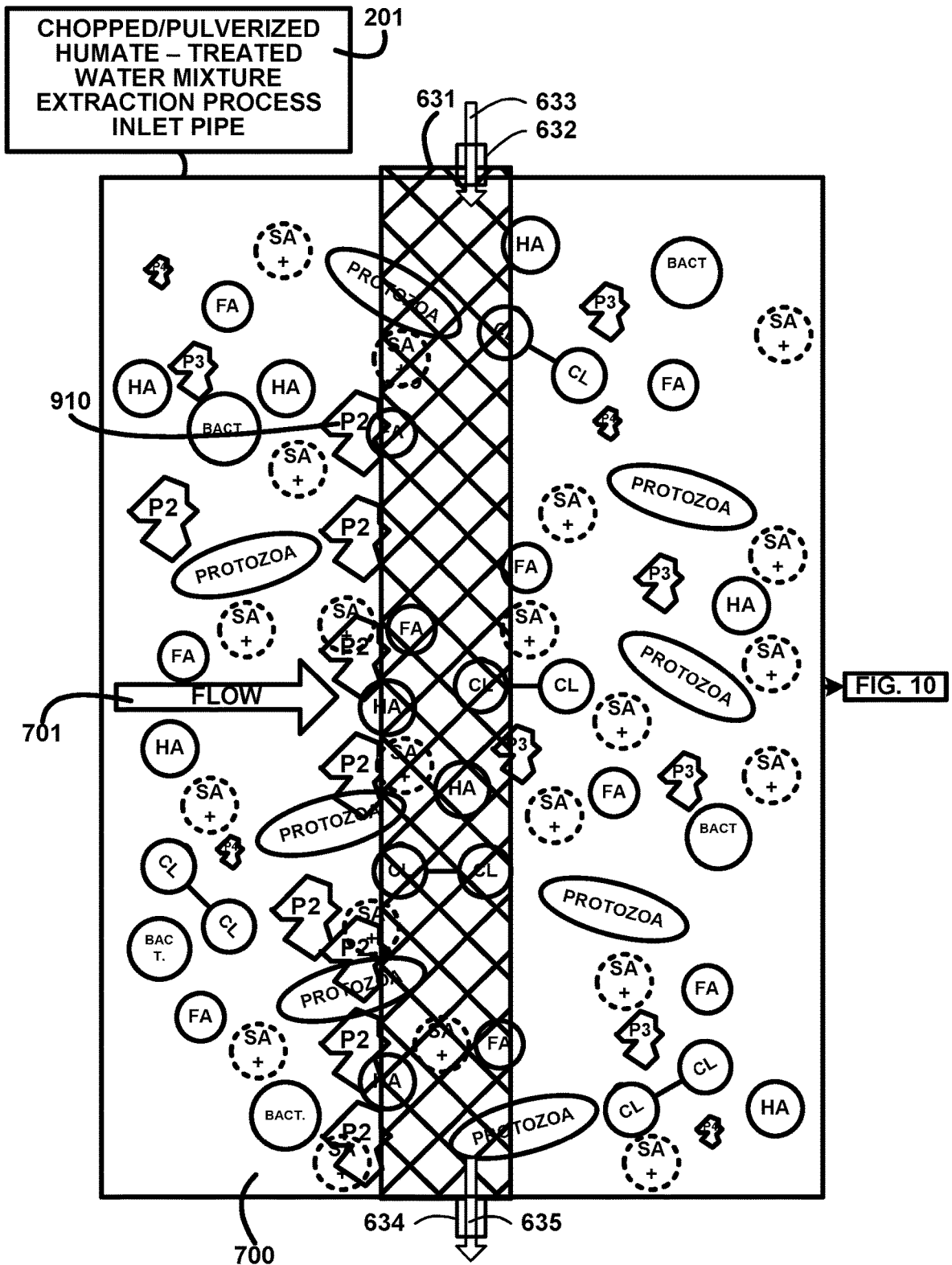
FIG. 9 shows for illustrative purposes only an example of second stage particulate filter of one embodiment.

Second Stage Particulate Filter:

FIG. 9 shows for illustrative purposes only an example of second stage particulate filter of one embodiment. FIG. 9 shows continuing from FIG. 8 the humate-treated water mixture supply piping 201 continue the flow 701 of the mixture through the second stage particulate filter 631 where p2 particulate size 2 are blocked 910 out of the chopped/pulverized humate-treated water mixture 700 of one embodiment. The description of the process continues on FIG. 10.

Figure 10:
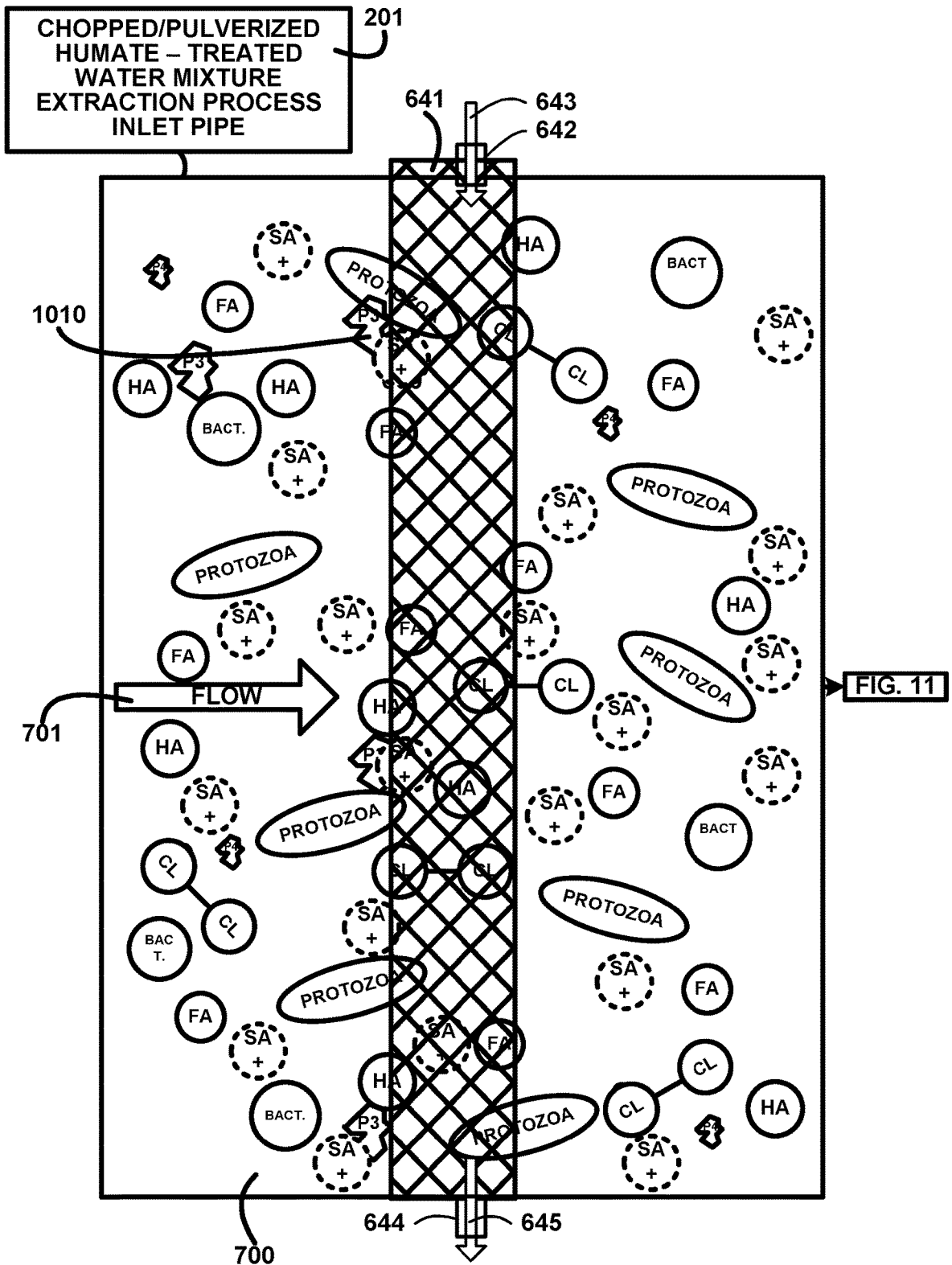
FIG. 10 shows for illustrative purposes only an example of third stage particulate filter of one embodiment.

Third Stage Particulate Filter:

FIG. 10 shows for illustrative purposes only an example of third stage particulate filter of one embodiment. FIG. 10 shows continuing from FIG. 9 the flow 701 through the humate-treated water mixture supply piping 201 through the third stage particulate filter 641 where p3 particulate size 3 are blocked 1010 out of the chopped/pulverized humate-treated water mixture 700 of one embodiment. The description of the process continues on FIG. 11.

Figure 11:
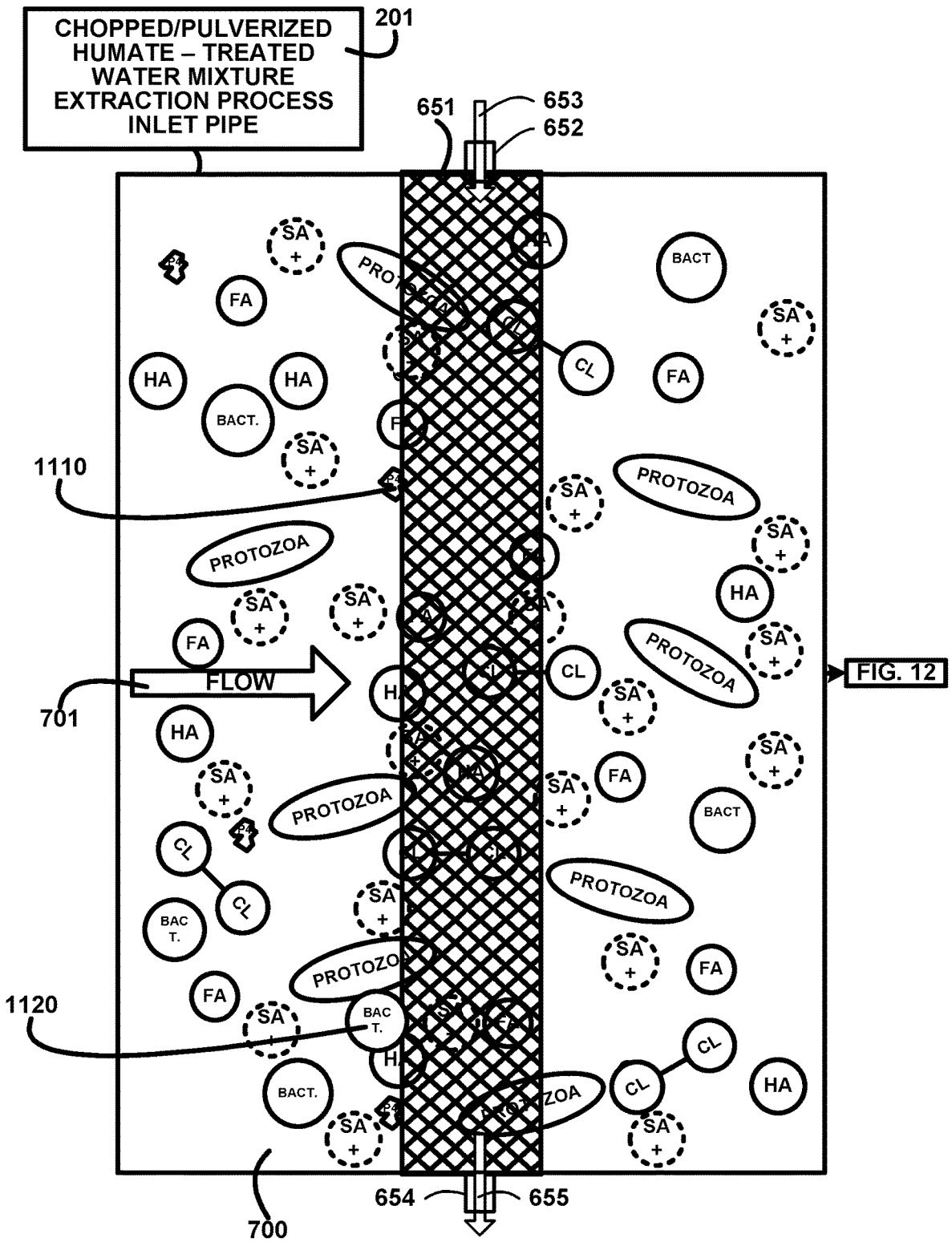
FIG. 11 shows for illustrative purposes only an example of fourth stage particulate filter of one embodiment.

Fourth Stage Particulate Filter:

FIG. 11 shows for illustrative purposes only an example of fourth stage particulate filter of one embodiment. FIG. 11 shows continuing from FIG. 10 humate-treated water mixture supply piping 201 continuing the flow 701 to pass through fourth stage particulate filter 651 where p4 particulate size 4 are blocked 1110 out of the chopped/pulverized humate-treated water mixture 700 of one embodiment. The description of the process continues on FIG. 12.

Figure 12:
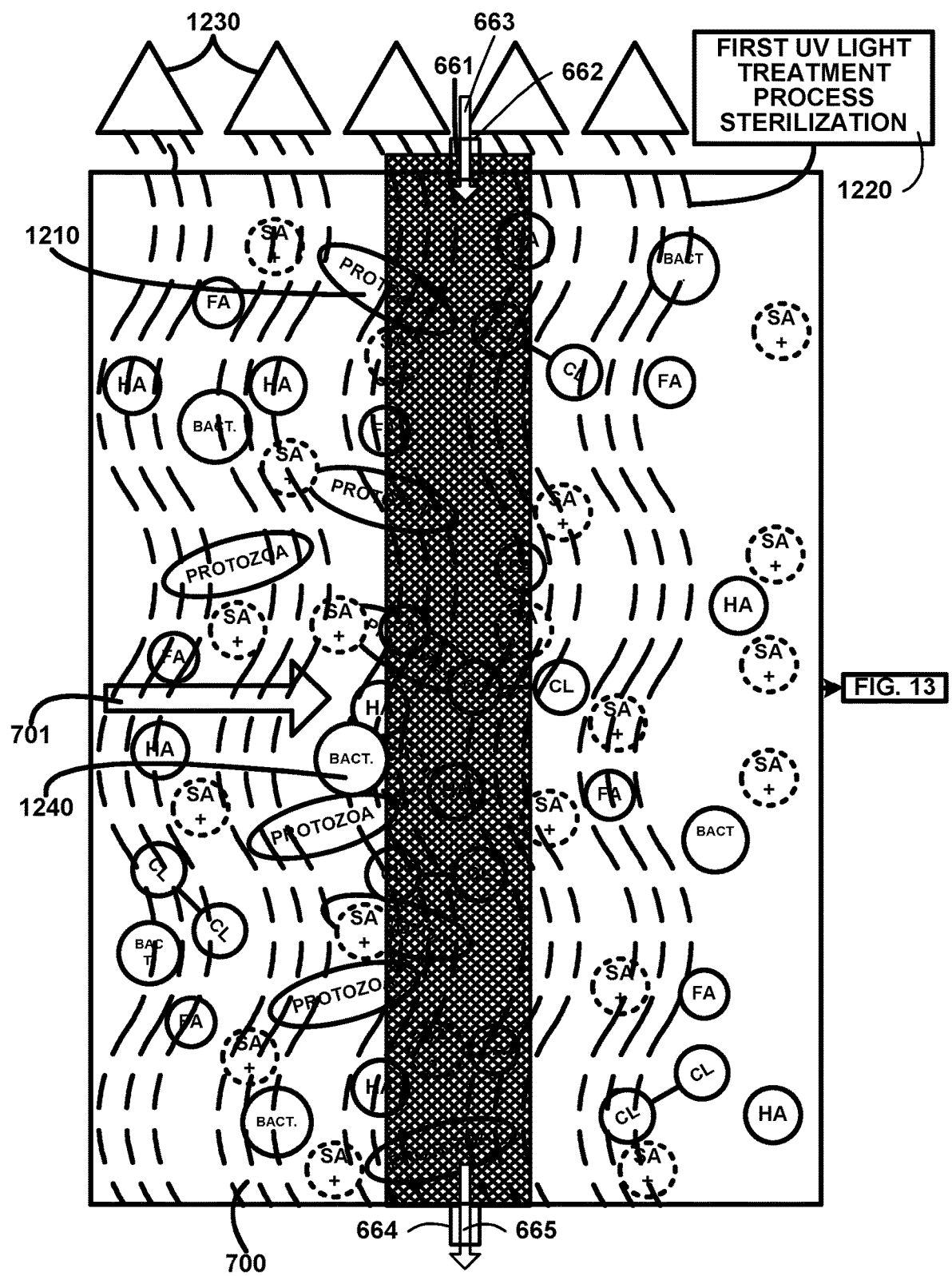
FIG. 12 shows for illustrative purposes only an example of fifth stage particulate filter of one embodiment.

Fifth Stage Particulate Filter:

FIG. 12 shows for illustrative purposes only an example of fifth stage particulate filter of one embodiment. FIG. 12 shows continuing from FIG. 11 the flow 701 passing through the humate-treated water mixture supply piping 201 to and through the fifth stage particulate filter 661. The mixture is also processed using the first UV light treatment process sterilization 1220 where bact. bacteria microorganism are killed and blocked 1240 and protozoa microorganism are killed and blocked 1210 out of chopped/pulverized humate-treated water mixture 700. The first UV light treatment process sterilization 1220 includes first UV light treatment devices 1230 to produce beam of the UV light for penetrating the mixture and killing the bacteria microorganisms and protozoa microorganisms of one embodiment. The description of the process continues on FIG. 13.

Figure 13:
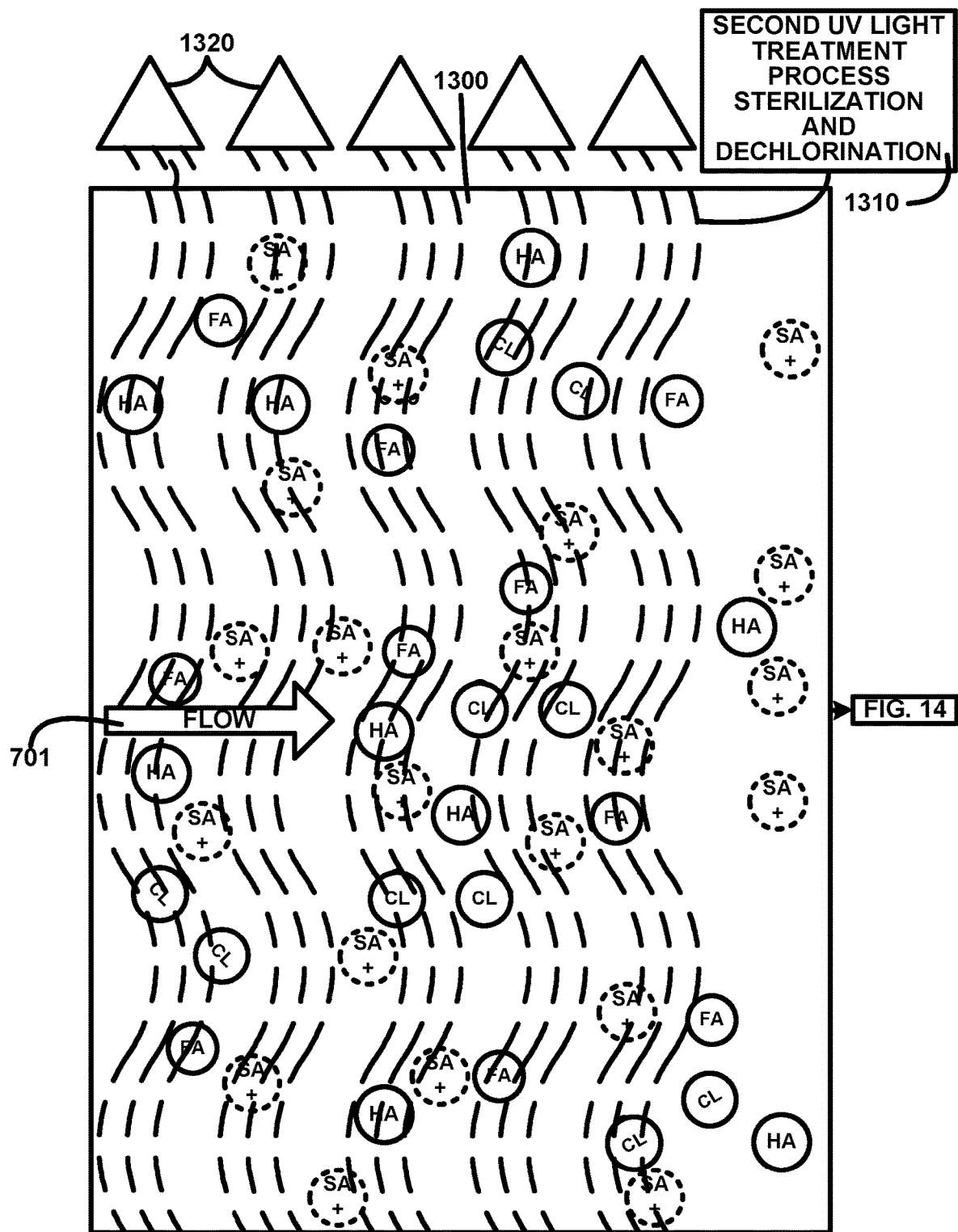
FIG. 13 shows for illustrative purposes only an example of second UV light treatment process sterilization and dechlorination of one embodiment.

Second UV Light Treatment Process Sterilization and Dechlorination:

FIG. 13 shows for illustrative purposes only an example of second UV light treatment process sterilization and dechlorination of one embodiment. FIG. 13 shows a continuation from FIG. 12 a second UV light treatment process sterilization and dechlorination 1310. A first post filtration chopped/pulverized humate-treated water mixture 1300 is passed through UV light beams created using second UV light treatment devices 1320 to expose the chopped/pulverized humate-treated water mixture 700 flow 701 to a higher intensity than the first UV light treatment process sterilization 1220 of FIG. 12 to kill any residual microorganism and to break apart chlorine Cl.sub.2 molecules of one embodiment. The description of the process continues on FIG. 14.

Figure 14:
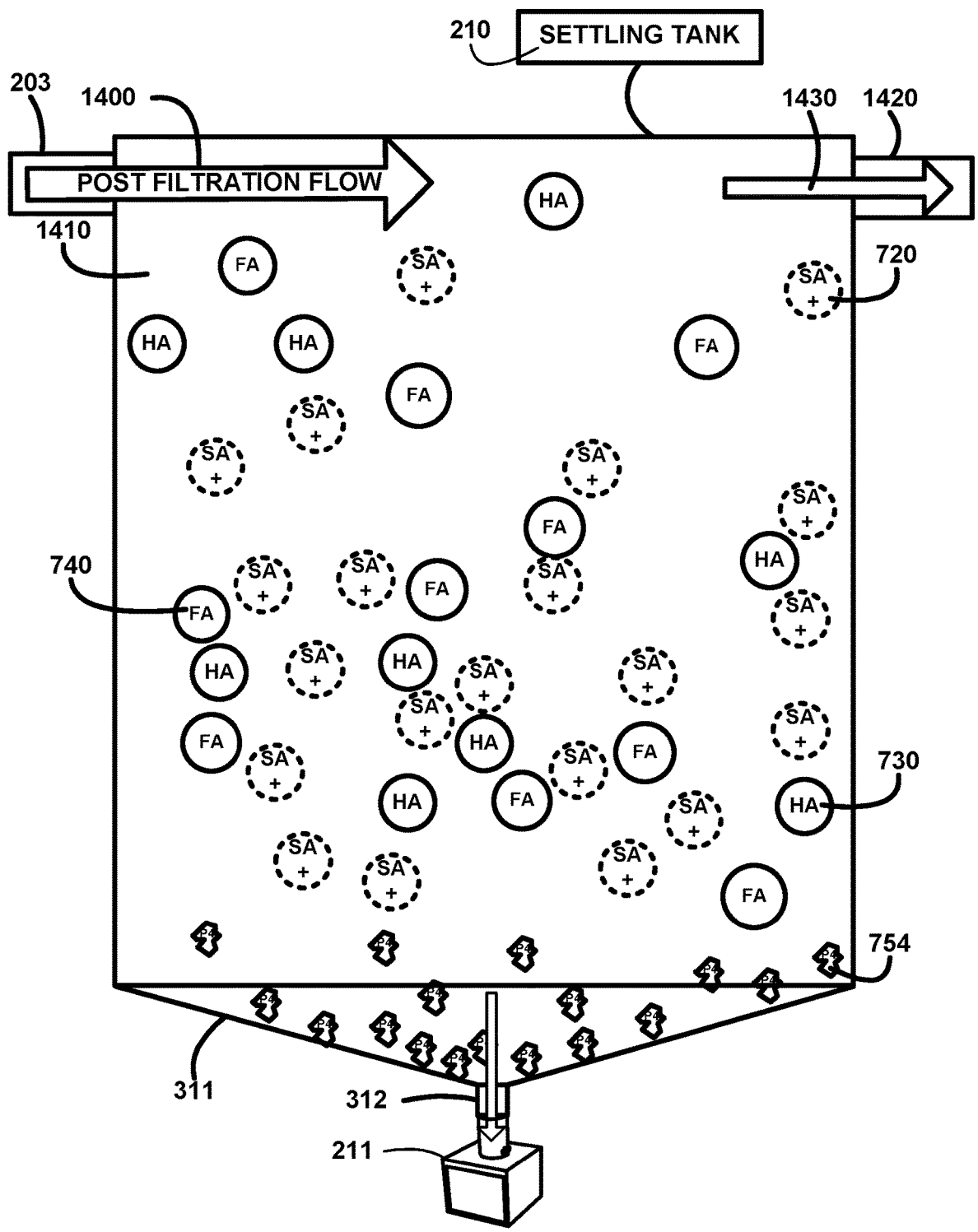
FIG. 14 shows for illustrative purposes only an example of a particulate filter settling tank of one embodiment.

Particulate Filter Settling Tank:

FIG. 14 shows for illustrative purposes only an example of a particulate filter settling tank of one embodiment. FIG. 14 shows a particulate filter settling tank 210 receiving the post filtration flow 1400 from the filtered humate-treated water mixture supply 203. The mixture 1410 includes pH treated water with suspended s+ soda ash molecules 720, HA humic acid molecules 730 and FA fulvic acid molecules 740. After filtration there may be residual suspended particulates p4 particulate size 4 754 or smaller in the mixture. The post filtration flow 1400 velocity slows when entering the settling tank 210. The reduced velocity allows residual suspended particulates to settle to the bottom of the settling tank 210 where the particulate waste accumulator funnel 311 accumulates the settled particulates and allows them to flow through the particulate waste disposal discharge pipe 312 and into the particulate disposal container 211. The remaining post filtration flow that is a settled humic-fulvic suspended mixture free of residual suspended particulates at the top of the settling tank 210 flows out 1430 of a settled humic-fulvic suspended mixture discharge pipe outlet 1420 of one embodiment.

Figure 15:
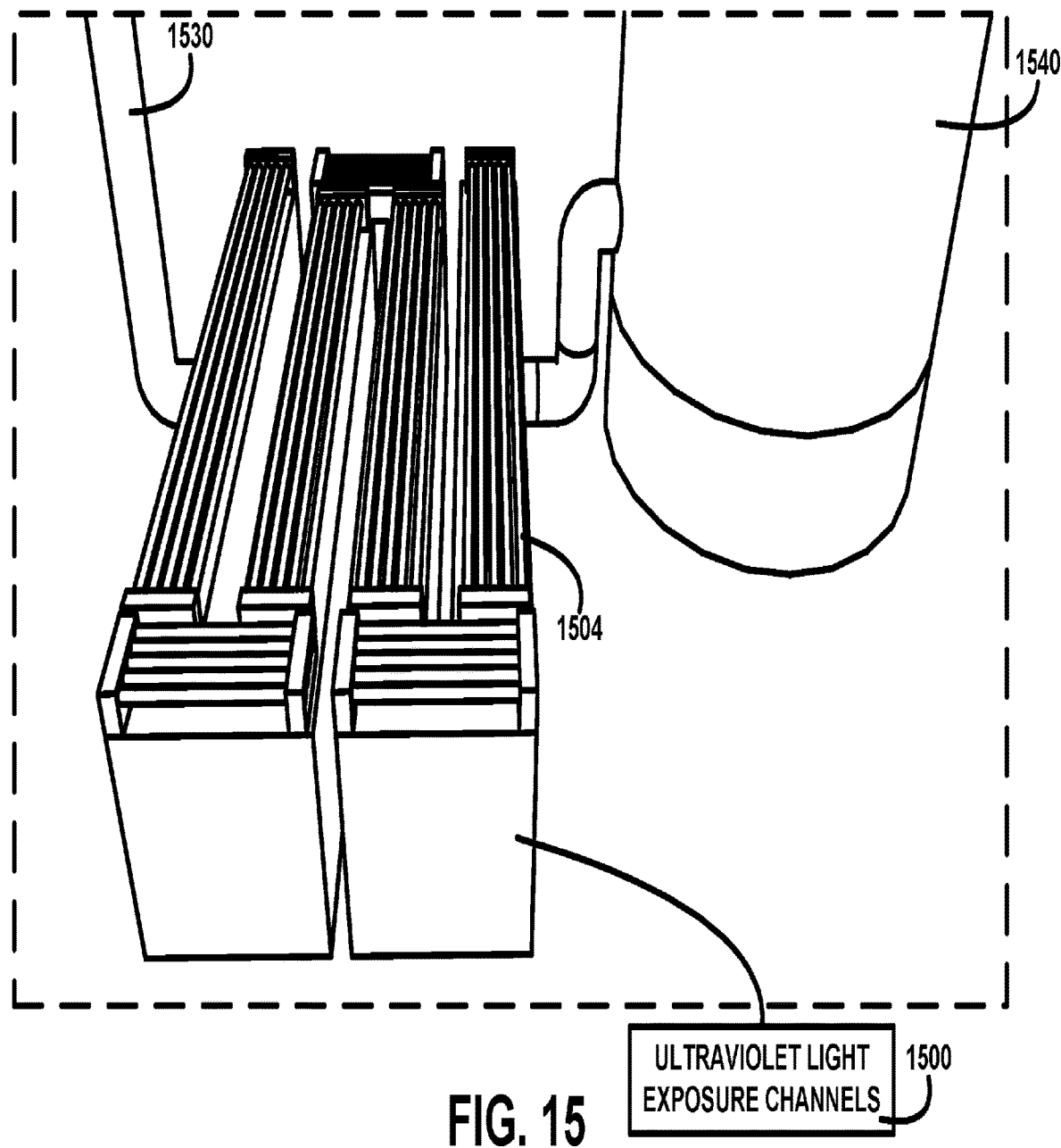
FIG. 15 shows for illustrative purposes only an example of ultraviolet light exposure channels of one embodiment.

Ultraviolet Light Exposure Channels:

FIG. 15 shows for illustrative purposes only an example of ultraviolet light exposure channels of one embodiment. FIG. 15 shows a settled humic-fulvic suspended mixture supply pipe 1530 supplying settled humic-fulvic suspended mixture to ultraviolet light exposure channels 1500. The ultraviolet light exposure bulbs 1504 are mounted to project UV light beams through the settled humic-fulvic suspended mixture flowing in the ultraviolet light exposure channels 1500. The ultraviolet light exposure bulbs 1504 and devices can include National Science Foundation (NSF) Certified UV Light Systems. The serpentine channel layout prolongs the time of the exposure to the fluid. The ultraviolet light exposure channels 1500 convey the exposed fluid into the first stage adsorption defluoridation device 230 of one embodiment.

Figure 16A:
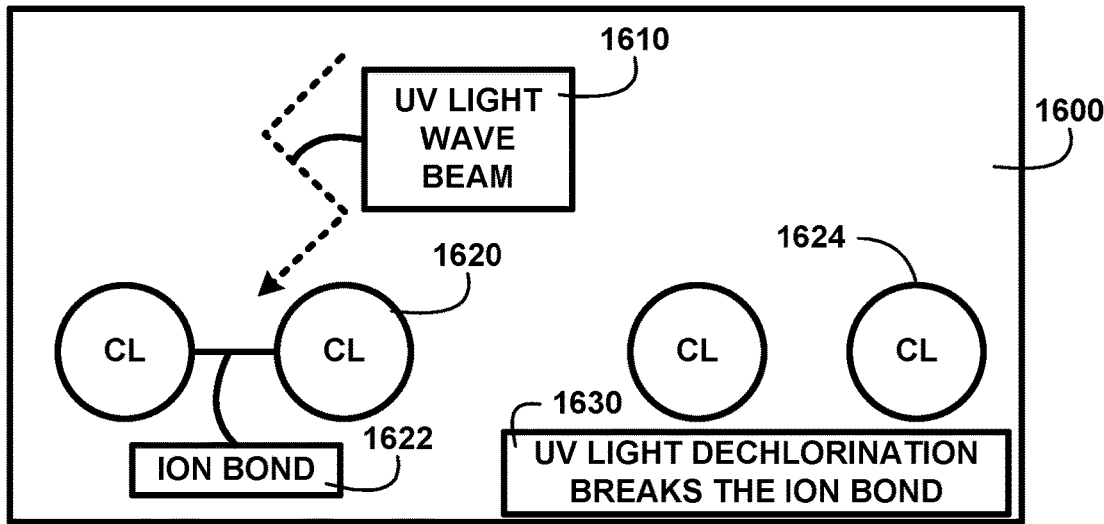
FIG. 16A shows for illustrative purposes only an example of UV light dechlorination of one embodiment.

UV Light Dechlorination:

FIG. 16A shows for illustrative purposes only an example of UV light dechlorination of one embodiment. FIG. 16A shows a UV light dechlorination 1600 process that projects at least one UV light wave beam 1610 into the mixture where chlorine has been detected. A chlorine $Cl_2$ molecule 1620 is held together by the force of an ion bond 1622. UV light dechlorination breaks the ion bond 1630 causing the two to separate into two free chlorine CI molecules 1624 that will dissipate more readily of one embodiment.

Figure 16B:
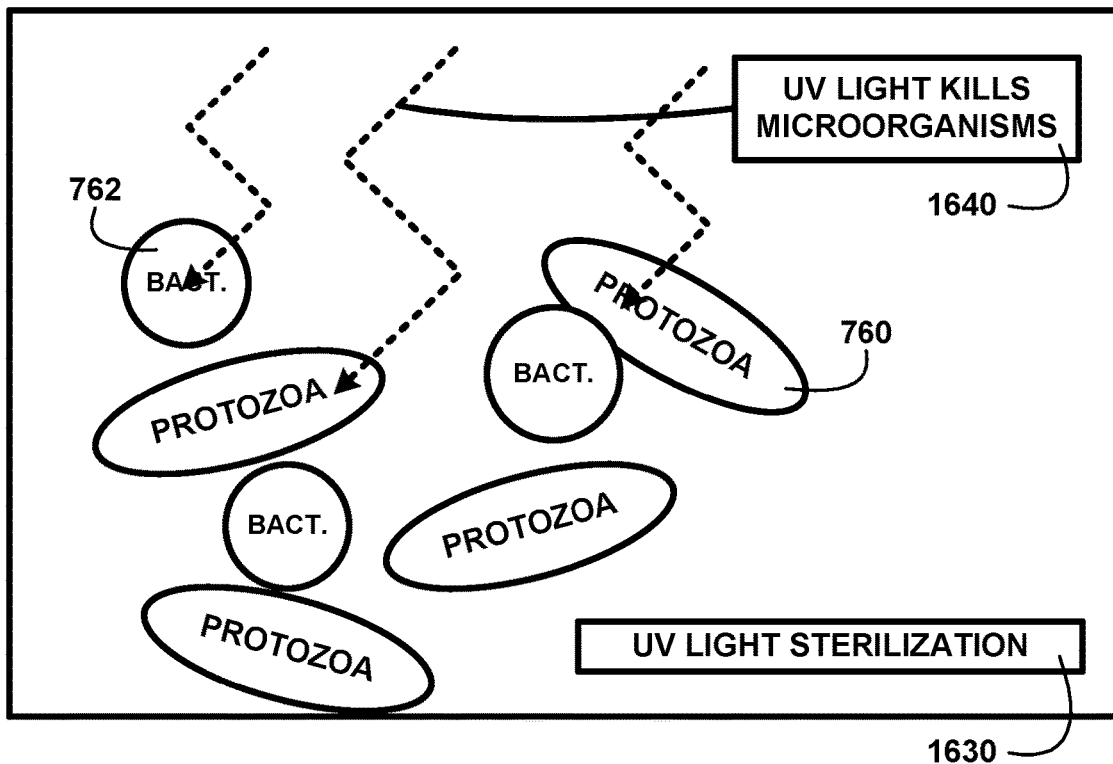
FIG. 16B shows for illustrative purposes only an example of UV light sterilization of one embodiment.

UV Light Sterilization:

FIG. 16B shows for illustrative purposes only an example of UV light sterilization of one embodiment. FIG. 16B shows a UV light sterilization 1630 process wherein UV light kills microorganisms 1640. For example the UV light wave beam intensity can kill the protozoa microorganism 760 and the bact. bacteria microorganism 762 and virus microorganisms of one embodiment.

Figure 17B:
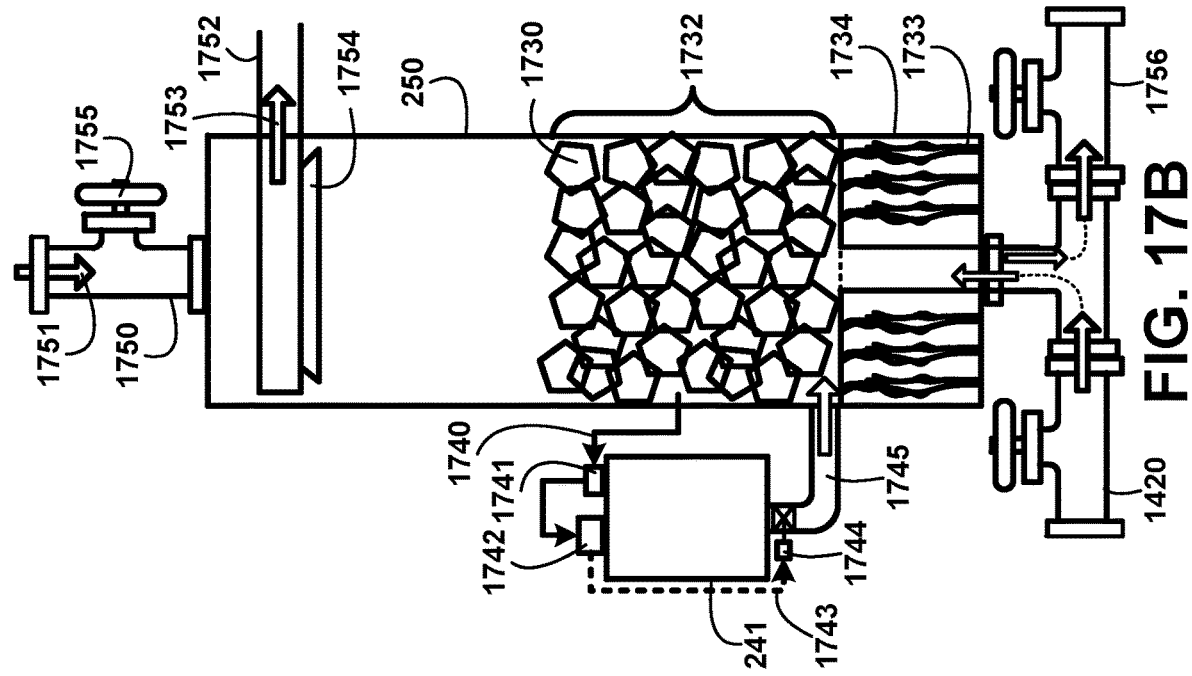
FIG. 17B shows for illustrative purposes only an example of a humic-fulvic acid separation chamber of one embodiment.
Figure 17A:
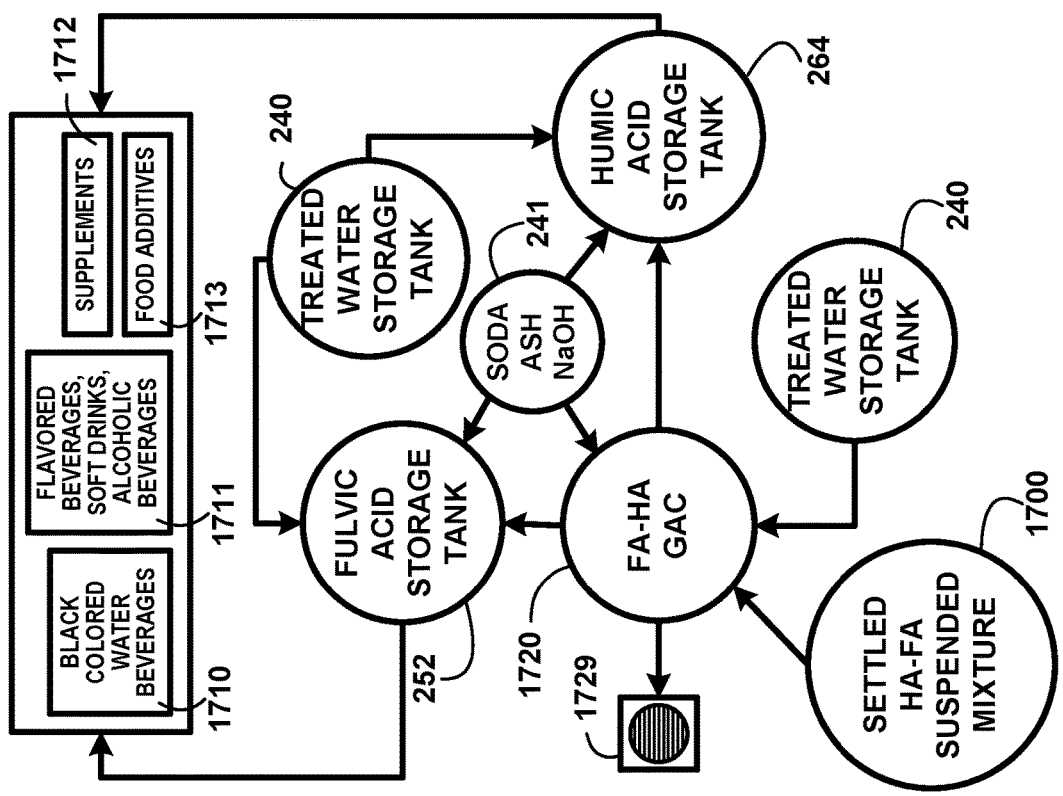
FIG. 17A shows for illustrative purposes only an example of a humic acid and fulvic acid separation and segregation process overview of one embodiment.

Settled Humic-Fulvic Suspended Mixture:

FIG. 17A shows for illustrative purposes only an example of a humic acid and fulvic acid separation and segregation process overview of one embodiment. FIG. 17 shows a settled HA-FA suspended mixture storage tank 1700 supplying the settled humic-fulvic suspended mixture to a fulvic acid—humic acid granular activated carbon (GAC) FA-HA GAC separation chamber 1720. Humic acid molecules adsorb to the granular activated carbon surfaces. When the separation and segregation processes are completed the remaining mixture and fresh flushing treated water are disposed of through discharge pipe and drain 1729 for recycling of one embodiment.

The separation process concentrates the fulvic acid molecules and segregates them to the fulvic acid storage tank 252 with temperature and pH control device 241. After the segregation of the fulvic acid molecules the humic acid molecules are separated from the granular activated carbon and are concentrated at the top of the separation chamber where they are segregated to the humic acid storage tank 264 with temperature and pH control device 241 of FIG. 2. A fresh treated water storage tank 240 with temperature control device and pH control device 241 supplies additional treated water when desired. The supplies of the fulvic acid molecules and humic acid molecules are used in the preparation products for human consumption including water beverages, flavored beverages, alcoholic beverages, and supplements and food additives of one embodiment.

Humic-Fulvic Acid Separation Chamber:

FIG. 17B shows for illustrative purposes only an example of a humic-fulvic acid separation chamber of one embodiment. FIG. 17B shows a humic-fulvic acid separation chamber 250 with the settled humic-fulvic suspended mixture flowing into the separation chamber through the settled humic-fulvic suspended mixture discharge pipe outlet 1420. The settled humic-fulvic suspended mixture fills the separation chamber above the fulvic acid segregation vacuum device 1754 and covers the vacuum draw pipe 1752. A bed 1732 of activated carbon 1730 provides surface area to attract the humic acid molecules. The fulvic acid molecules rise to the top section of the separation chamber where they are drawn out of the separation chamber using the separation vacuum device 1754 to the fulvic acid storage tank 252 of FIG. 2 with temperature and pH control devices. When the concentration fulvic acid molecules is depleted from the settled humic-fulvic suspended mixture as indicated using a fulvic acid sensor the pH control device 241 is used to draw a sample of the mixture 1740 into a sensor 1741 to detect the pH level of the mixture.

A digital processor 1742 is used to calculate the volume of base to inject into the mixture 1745 to adjust the pH level and transmit a signal 1743 using a solenoid 1744 to open a valve to aid in the release of the humic acid molecules from the activated carbon surfaces. Burners 1733 included in a temperature control device 1734 are automatically ignited to raise the temperature of the remaining mixture to further aid in the release of the humic acid molecules from the activated carbon surfaces. The humic acid molecules rise to the top of the separation chamber and are draw out to the humic acid storage tank 264 of FIG. 2 with temperature and pH control devices. After segregation of the humic acid molecules a valve 1755 is opened to flush the separation chamber with fresh treated water 1751 through an inlet pipe 1750 to regenerate the activated carbon material 1730. The flushing regeneration water mixture is drained out the disposal discharge pipe 1756 for recycling of one embodiment.

Figure 17C:
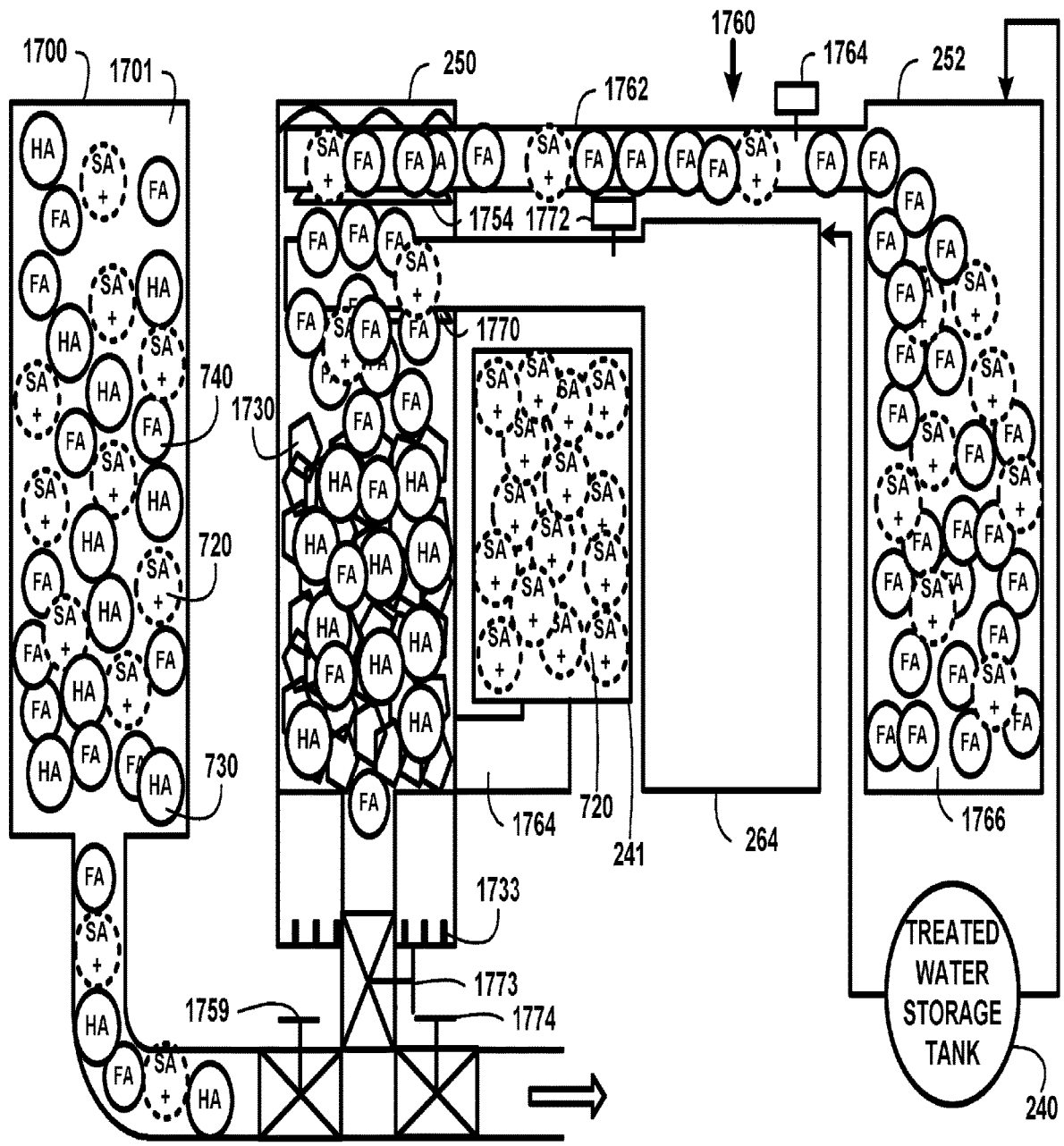
FIG. 17C shows for illustrative purposes only an example of fulvic acid separation and segregation of one embodiment.

Fulvic Acid Separation and Segregation:

FIG. 17C shows for illustrative purposes only an example of fulvic acid separation and segregation of one embodiment. FIG. 17C shows the presence of SA+ soda ash molecule 720, humic acid molecule 730, fulvic acid molecule 740 in a settled humic-fulvic suspended mixture supply 1701 in a settled HA-FA suspended mixture storage tank 1700. Piping conveying the mixture 1759 through an opened settled humic-fulvic suspended mixture supply valve 1759 and through an opened humic-fulvic acid separation chamber inlet valve 1773 for an activated carbon HA separation process 1760 of one embodiment.

The humic-fulvic acid separation chamber 250 contains a quantity of activated carbon 1730. When the humic-fulvic acid separation chamber 250 is filled to the top the settled humic-fulvic suspended mixture supply valve 1759 and humic-fulvic acid separation chamber inlet valve 1773 are closed. Humic acid molecules attach to the surfaces of the activated carbon. Fulvic acid molecules rise to the top of the separation chamber. A vacuum segregation of fulvic acid molecules 1762 is performed using a fulvic acid segregation vacuum device 1754. The fulvic acid segregation vacuum device 1754 draws the concentration fulvic molecules into the fulvic acid storage tank 252. Fulvic acid molecules suspended in treated water storage tank 1766 show in the fulvic acid storage tank 252. A fulvic acid detection device 1764 detects and measures the concentration of fulvic acid molecules. When the fulvic acid detection device 1764 measurements indicate the concentration fulvic acid molecules is depleted the fulvic acid segregation process stops of one embodiment.

Also showing is a humic acid molecules vacuum device 1770, humic acid detection device 1772, humic acid storage tank 264, pH control device 241, pH control device injection piping 1764, burners 1733, fresh treated water storage tank 240 and a humic-fulvic acid separation chamber discharge valve 1774 closed of one embodiment.

Figure 17D:
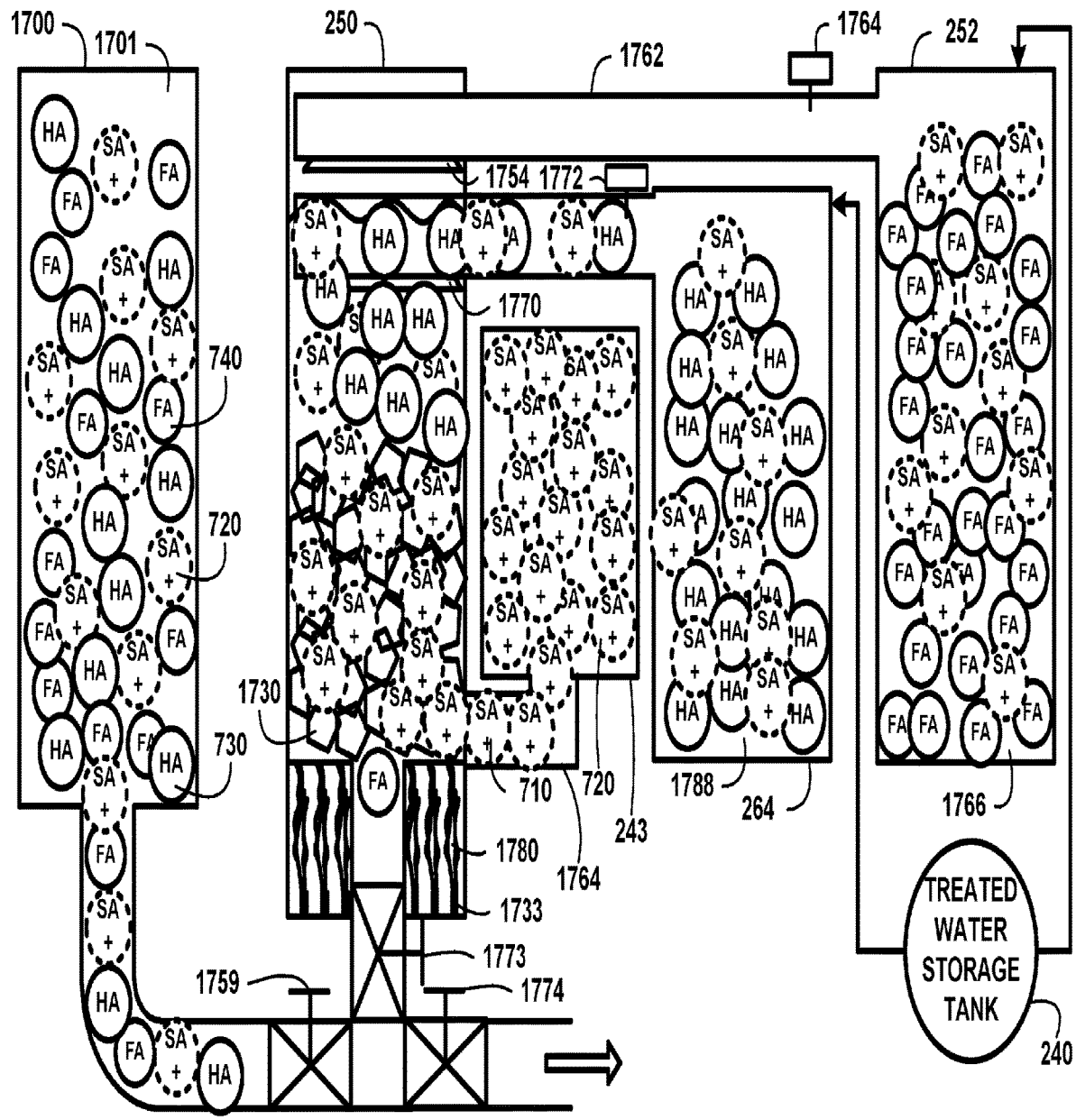
FIG. 17D shows for illustrative purposes only an example of humic acid separation and segregation of one embodiment.

Humic Acid Separation and Segregation:

FIG. 17D shows for illustrative purposes only an example of humic acid separation and segregation of one embodiment. FIG. 17D shows the presence of SA+ soda ash molecule 720, humic acid molecule 730, and fulvic acid molecule 740 in a settled humic-fulvic suspended mixture supply 1701 in a settled HA-FA suspended mixture storage tank 1700. Piping conveying the mixture 1759 through an opened settled humic-fulvic suspended mixture supply valve 1759 and through an opened humic-fulvic acid separation chamber inlet valve 1773 for an activated carbon HA separation process 1760. The humic-fulvic acid separation chamber 250 shows the activated carbon 1730 with attached humic acid molecules. The pH control device 241 with pH control device injection piping 1764 begins a process for injecting soda ash to raise pH 710. The burners 1733 are activated for ignited burners to raise the temperature 1780 of the mixture. Humic acid molecules are desorbed from the activated carbon and humic acid molecules rise to the top of the separation chamber.

A humic acid molecules vacuum device 1770 draws the concentrated humic acid molecules into the humic acid storage tank 264. Humic acid molecules suspended in treated water storage tank 1788 are showing in the humic acid storage tank 264. The humic acid detection device 1772 detects and measures the concentration of humic acid molecules in the humic acid molecules vacuum device 1770 flow. When the humic acid detection device 1772 measurements indicate the concentration humic acid molecules is depleted the humic acid segregation process stops. Also showing are the vacuum segregation of fulvic acid molecules 1762, fulvic acid molecules suspended in treated water storage tank 1766, fulvic acid detection device 1764, fulvic acid storage tank with temperature and pH control devices 252, and fulvic acid segregation vacuum device 1754 of one embodiment.

Figure 18A:
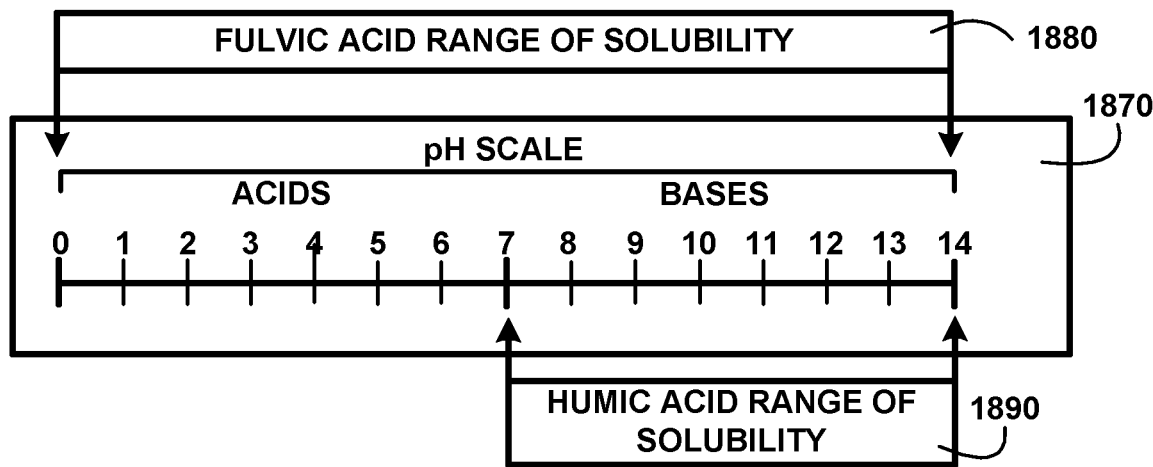
FIG. 18A shows for illustrative purposes only an example of a pH scale of one embodiment.

The process continues with a flushing process wherein fresh treated water is pumped into the humic-fulvic acid separation chamber 250 from the fresh treated water storage tank 240. The humic-fulvic acid separation chamber inlet valve 1773 and humic-fulvic acid separation chamber discharge valve 1774 are opened for discharging the remaining mixture and flush treated water for recycling of one embodiment.

pH Scale:

FIG. 18A shows for illustrative purposes only an example of a pH scale of one embodiment. FIG. 18A shows a pH scale 1870. The pH scale shows the ranges of pH are from 0 to 14. A humic acid range of solubility pH 7 to 14 1890 is limited to a base pH level. A fulvic acid range of solubility pH 0 to 14 means it can be soluble at any pH level.

Figure 18B:
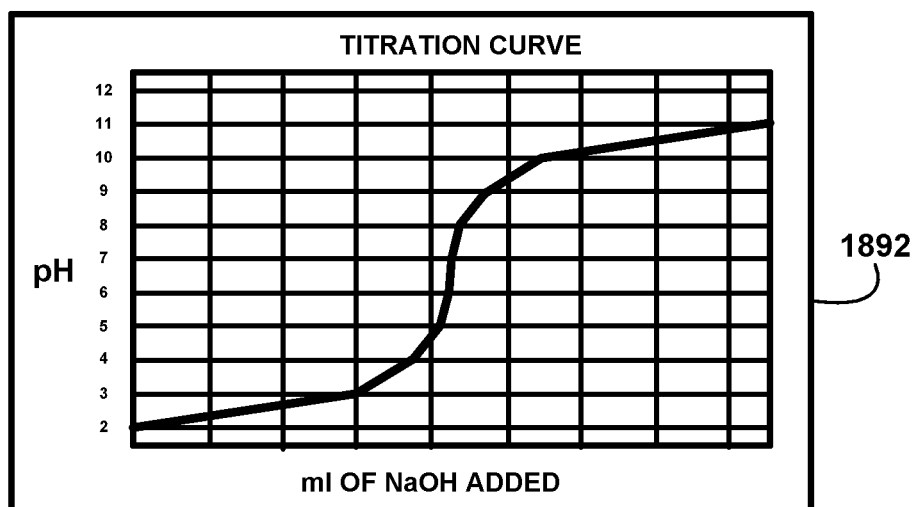
FIG. 18B shows a block diagram of an overview flow chart of titration curve of one embodiment.

Titration Curve:

FIG. 18B shows a block diagram of an overview flow chart of titration curve of one embodiment. FIG. 18B shows a titration curve 1892. Sodium hydroxide NaOH also called Soda Ash (SA) is a base material that when various amounts of ml of NaOH added to a solution raises the pH level from pH levels 2 to 12 based on the number of milliliters of NaOH added to the solution. The black water humic and fulvic acids extraction for human consumption method and devices uses at least one automated periodic sampling of the humate-treated water mixture at points along the process to check the pH level. If the pH is lower that a desired level NaOH is added to the solution in predetermined amounts to increase the base pH level to the desired level from the sampling detected level.

Figure 19A:
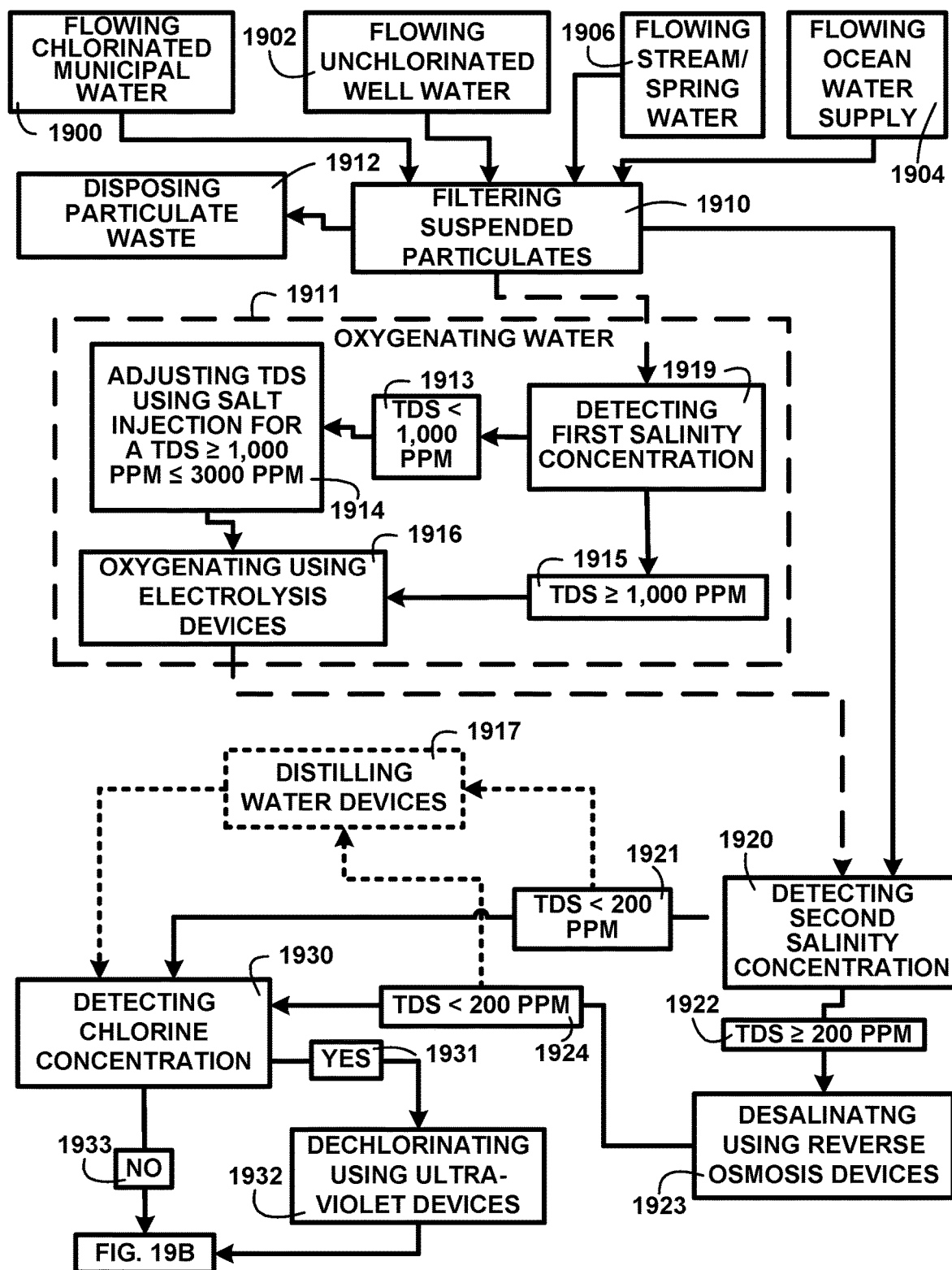
FIG. 19A shows a block diagram of an overview flow chart of treating water processes of one embodiment.

Treating Water Processes:

FIG. 19A shows a block diagram of an overview flow chart of treating water processes of one embodiment. FIG. 19A shows flowing chlorinated municipal water 1900, flowing unchlorinated well water 1902, flowing stream/spring water 1906, and flowing ocean water supply 1904 as water sources that may be used for the treating water processes. At least one of the water sources is processed for filtering suspended particulates 1910. The particulates removed are conveyed for disposing particulate waste 1912.

A next process can include a process for oxygenating water 1911 beginning with a process for detecting first salinity concentration 1919. Oxygenating water 1911 can include an electrolysis process of water with a salinity level to promote conductivity of the electrolysis charges through the volume of water. A detecting first salinity concentration 1919 process determines the salinity of the water. Should the water have a total dissolved salt (TDS) concentration where TDS<1,000 ppm 1913 the process continues for adjusting TDS using salt injection for a TDS.Itoreq. 1,000 ppm 3000 ppm 1914 and the water is automatically diverted for oxygenating using electrolysis devices 1916. If the detecting first salinity concentration 1919 process determines the salinity of the water has TDS.gtoreq. 1,000 ppm 1915 the water is automatically diverted for oxygenating using electrolysis devices 1916. After an oxygenating water 1911 process is complete the salinity of the water can be reduced to a suitable drinking water concentration level.

A next process can include a process for detecting second salinity concentration 1920 of the water source. Total dissolved salt (TDS) is a measure of the salts suspended in liquid generally measured in parts per million (ppm). The black water humic and fulvic acids extraction for human consumption method and devices targets TDS<200 ppm 1921 for human consumption which is a level generally found in drinking water. Automated sampling of the water source is used for obtaining a sample that is fed into an automated chemical analyzer for detecting salinity concentration 1920. A TDS<200 ppm 1921 automatically initiates a diversion of the flow of the water source to the next process. A TDS.gtoreq.200 ppm 1922 automatically initiates a diversion of the flow of the water source for desalinating using reverse osmosis devices 1923 to reduce the salinity to a TDS<200 ppm 1924. Once the analysis reaches a salinity of a TDS<200 ppm 1921 the flow is automatically diverted to a next process.

A next process can include creating distilled water using distilling water devices 1917. After a distilling water process is complete the process continues to a process for detecting chlorine concentration 1930.

A next process can include a process for detecting chlorine concentration 1930. A detected chlorine concentration with a yes 1931 or positive for the presence of chlorine (Cl.sub.2) initiates an automatic diversion of the water source flow for dechlorinating using ultra-violet devices 1932. Upon complete of dechlorination the flow is automatically diverted to the next process. A detecting chlorine concentration 1930 with a result of no 1933 or negative detection the presence of chlorine automatically diverted to the additional processes described in FIG. 19B.

Figure 19B:
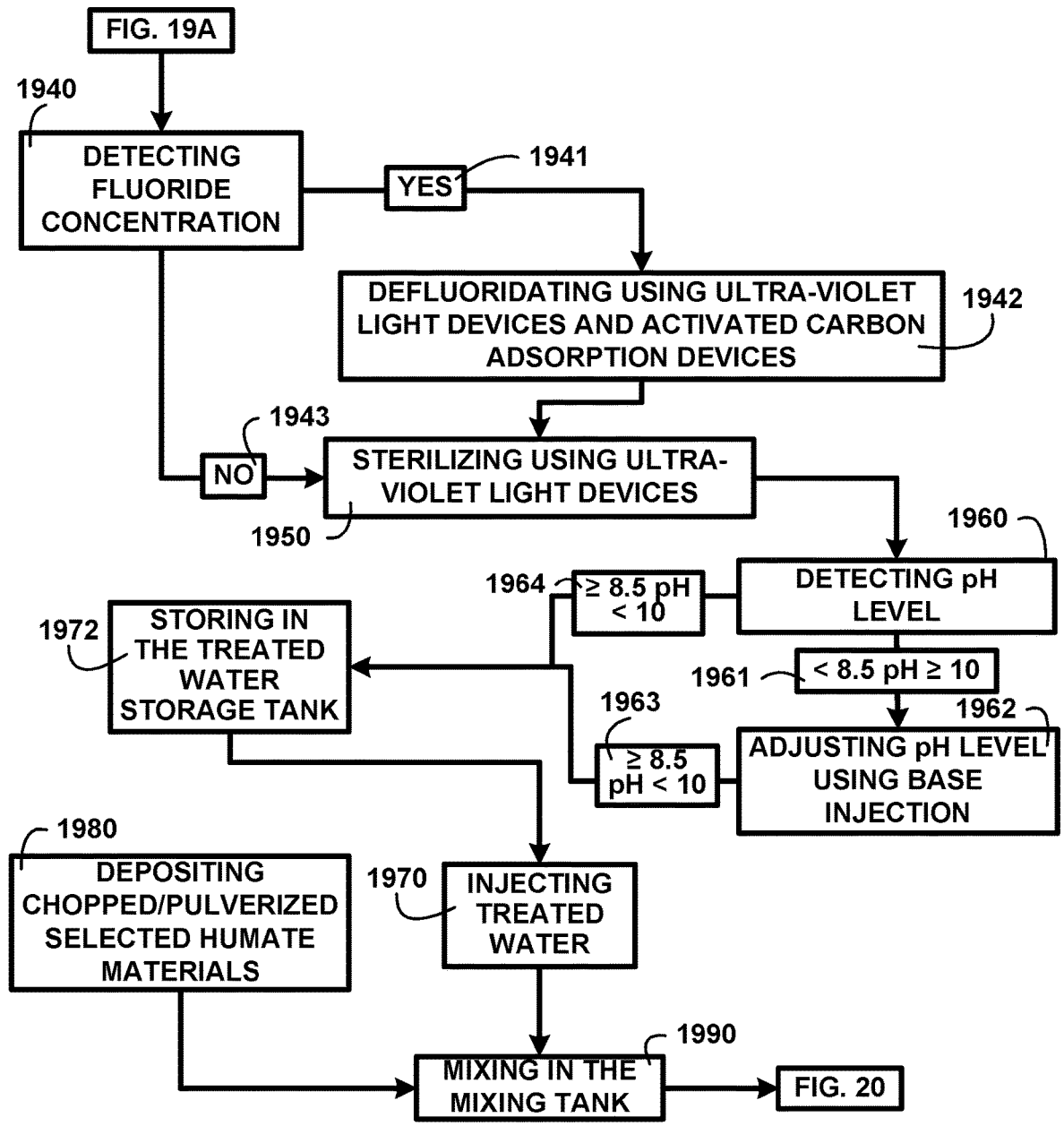
FIG. 19B shows a block diagram of an overview flow chart of treating water additional processes of one embodiment.

Treating Water Additional Processes:

FIG. 19B shows a block diagram of an overview flow chart of treating water additional processes of one embodiment. FIG. 19B shows treating water additional processes continuing from FIG. 19A including a process for detecting fluoride concentration 1940. A detecting fluoride concentration 1940 analysis result indication yes 1941 a positive detection of fluoride in the water source automatically diverts the flow of the water source to a process for defluoridating using ultra-violet light devices and activated carbon adsorption devices 1942. Once an automatic sampling analysis shows the defluoridation process is complete the water source flow is diverted to the next process. An initial detecting fluoride concentration 1940 analysis result indication no 1943 a negative finding that no fluoride is present the water source is diverted to the next process for sterilizing using ultra-violet light 1950.

A first step in the sterilizing using ultra-violet light devices 1950 process is automatically taking a sampling of the water source for detecting pH level 1960. An automatic detecting pH level 1960 result showing a <8.5 pH.gtoreq. 10 1961 automatically diverts the flow of the water source flow for adjusting pH level using base injection 1962. Once a .gtoreq.8.5 pH<10 1963 is detected after the adjusting pH level using base injection 1962 process the water source flow is automatically diverted for storing in the treated water storage tank 1972 for the next process. If the initial automatic detecting pH level 1960 shows a .gtoreq. 8.5 pH<10 1964 the water source flow is automatically diverted for storing in the treated water storage tank 1972 for the next process for injecting treated water 1970 for mixing in the mixing tank 1990. Once the treated water source is injected into the mixing tank 171 a process begins for depositing chopped/pulverized selected humate materials 1980 for mixing in the mixing tank 1990 with the injected treated water. The process descriptions continue in FIG. 20.

Figure 20:
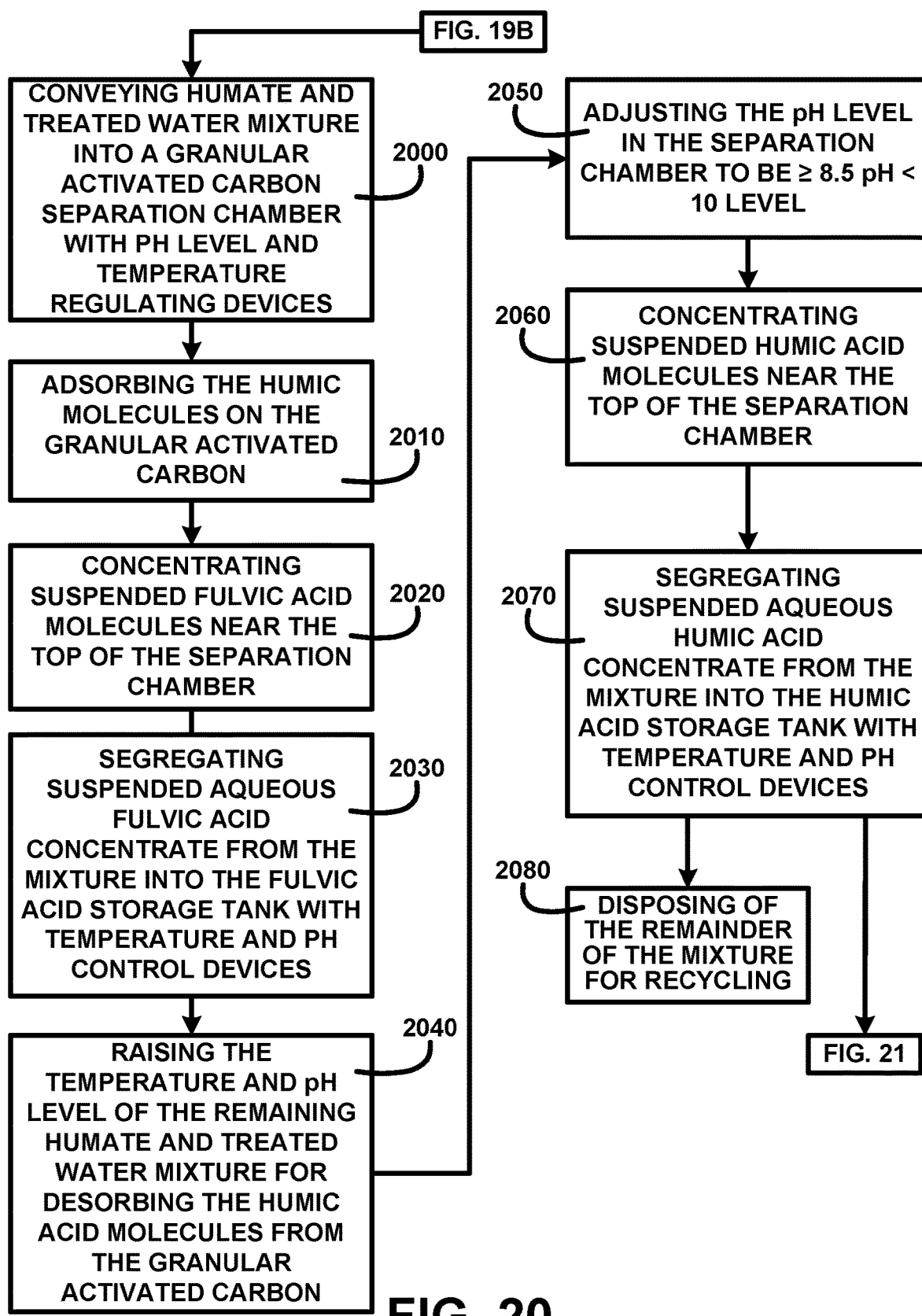
FIG. 20 shows a block diagram of an overview flow chart of extraction and segregation of humic and fulvic acids of one embodiment.

Extraction and Segregation of Humic and Fulvic Acids:

FIG. 20 shows a block diagram of an overview flow chart of extraction and segregation of humic and fulvic acids of one embodiment. FIG. 20 shows the continuation of the processing from FIG. 19 including conveying humate and treated water mixture into a granular activated carbon separation chamber with pH level and temperature regulating devices 2000. Adsorbing the humic molecules on the granular activated carbon 2010. Concentrating suspended fulvic acid molecules near the top of the separation chamber 2020 then segregating suspended aqueous fulvic acid concentrate from the mixture into the fulvic acid storage tank with temperature and pH control devices 2030. The aqueous fulvic acid concentrate having been removed the process continues by raising the temperature and pH level of the remaining humate and treated water mixture for desorbing the humic acid molecules from the granular activated carbon 2040. A sampling of the remaining humus and treated water mixture is automatically analyzed to determine the pH level. If the sampling is <8.5 pH.gtoreq. 10 the pH control device automatically initiates adjusting the pH level in the granular activated carbon separation chamber to be .gtoreq.8.5 pH<10 level 2050 and cause the release of the humic acid molecules from the activated carbon materials. Concentrating suspended humic acid molecules near the top of the separation chamber 2060. Segregating suspended aqueous humic acid concentrate from the mixture into the humic acid storage tank with temperature and pH control devices 2070. Disposing of the remainder of the mixture for recycling 2080. Description of the processing continues in FIG. 21.

Figure 21:
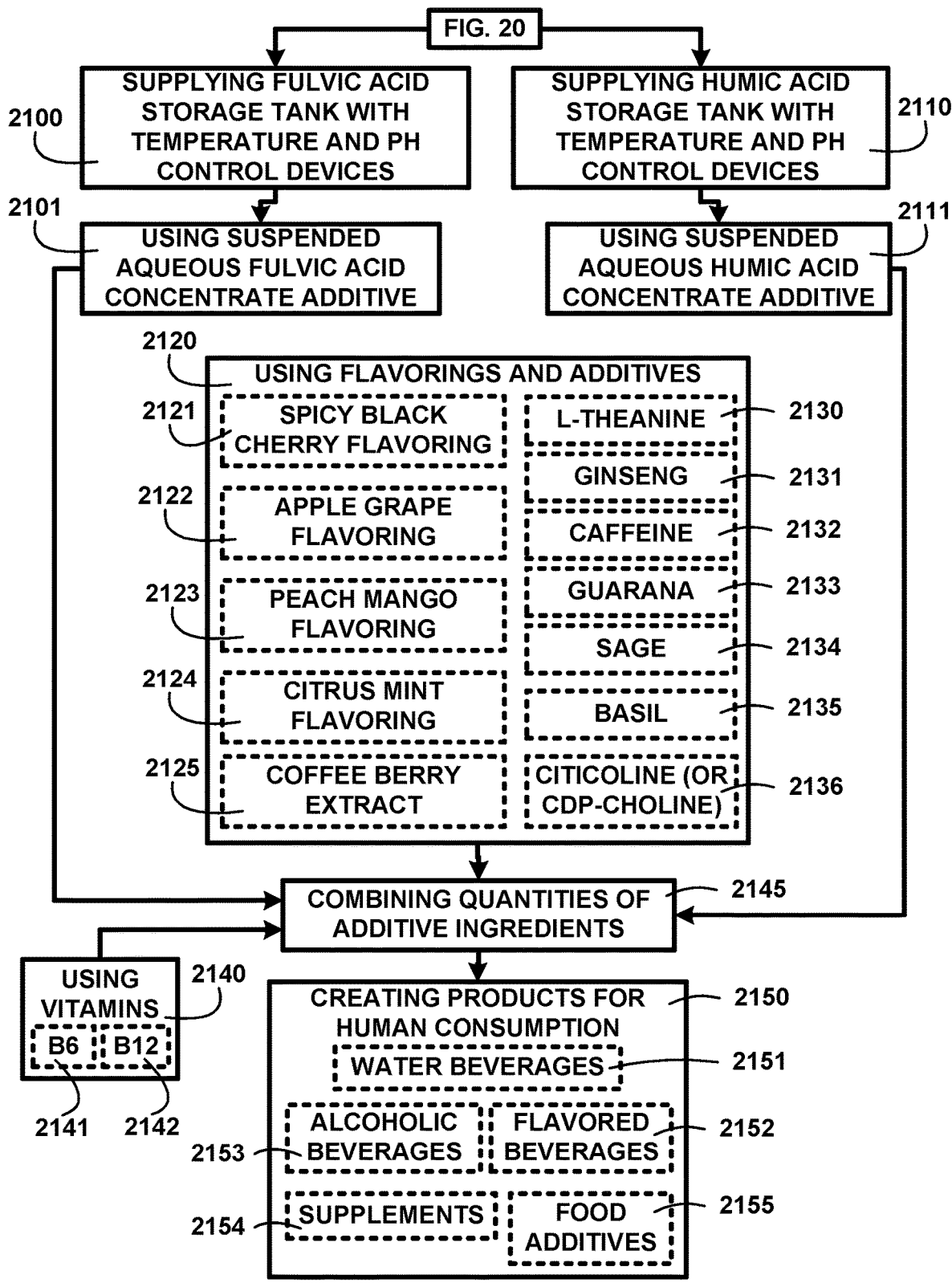
FIG. 21 shows a block diagram of an overview flow chart of creating products for human consumption with humic and fulvic acids of one embodiment.

Creating Products for Human Consumption:

FIG. 21 shows a block diagram of an overview flow chart of creating products for human consumption with humic and fulvic acids of one embodiment. FIG. 21 shows processing continuing from FIG. 20 with supplying fulvic acid storage tank with temperature and pH control devices 2100 and using suspended aqueous fulvic acid concentrate additive 2101. Processing includes supplying humic acid storage tank with temperature and pH control devices 2110 and using suspended aqueous humic acid concentrate additive 2111. Products for human consumption will also be using flavorings and additives 2120 including spicy black cherry flavoring 2121, apple grape flavoring 2122, peach mango flavoring 2123, citrus mint flavoring 2124, coffee berry extract 2125, L-theanine 2130, ginseng 2131, caffeine 2132, guarana 2133, sage 2134, basil 2135, citicoline (or CDP-choline) 2136, and other flavorings and additives 2120. The ingredients being used also include and using vitamins 2140 including vitamin B6 2141 and vitamin B12 2142 and other vitamins.

Combinations of the ingredients can produce different tastes and consumer benefits including improving a consumer's mood, vitamins and nutrients providing a consumer energy boost, improving a person focus, providing newly focused mental faculties, providing trace minerals that supply electrolytes, antioxidants and amino acids a consumer's body needs, helps boost a consumer's immune system and other benefits. Combining quantities of additive ingredients 2145 and selecting some but not all of the ingredients can be varied to target specific benefits and taste in the products for human consumption. Creating products for human consumption that include humic and fulvic acids includes water beverages 2151, flavored beverages 2152, alcoholic beverages 2153, supplements 2154 and food additives 2155. The black water humic and fulvic acids extraction for human consumption method and devices not only removes harmful chemicals in the processing but also does not use other chemicals that can pose a health risk to consumers of products that include humic and fulvic acids extracted using potentially harmful chemicals in the extraction processing.

One embodiment includes a method, including processing at least one water source supply including chlorinated municipal water, flowing unchlorinated well water, stream/spring water, and ocean water for treating the at least one water source including particulate filtering, detecting total dissolved salts, desalinating, detecting chlorine, dechlorinating, detecting fluoride, defluoridating, sterilizing, detecting pH level, and adjusting pH level .gtoreq.8.5 and <10 for mixing with extracted humic acid and fulvic acid; chopping and pulverizing at least one humate source including humus soil, coal, ocean water, inland stream water, and degradated plants; mixing the chopped and pulverized at least one humate source with the processed water product; processing the chopped and pulverized at least one humate source and the processed water product mixture to separate, segregate, suspend and store fulvic acid from the at least one humate source in a fresh quantity of the processed water product, and separate, segregate, suspend and store humic acid from the at least one humate source in a fresh quantity of the processed water product, and adjusting pH levels .gtoreq.8.5 and <10; and creating at least one or more beverage product including water beverage, flavored beverages, alcoholic beverages, and supplements and food additives for human consumption using the separated, segregated, suspended and stored fulvic acid, humic acids and other ingredients including vitamins.

It further includes processing the chopped and pulverized at least one humate source and the processed water product mixture to separate, segregate, suspend and store fulvic acid and humic acid from the at least one humate source includes a process for automatically sampling and detecting a pH level in the mixture using a vacuum coupled pipet and pH sensors and analyzing the sample using a chemical analyzer to determine the pH level in the mixture and using an automatic injection device to add a base material including soda ash NaOH to adjust the pH level to a pH level equal to or greater than 8.5 in the mixture for suspending the humic acid and fulvic acid molecules in a soluble state in the mixture. Processing the chopped and pulverized at least one humate source and the processed water product mixture to separate, segregate, suspend and store fulvic acid and humic acid from the at least one humate source includes a process using at least a five step particulate filtration device for segregating and removing solid particulates in the mixture including residual solid materials of the chopped and pulverized at least one humate source and microorganisms.

Processing the chopped and pulverized at least one humate source and the processed water product mixture to separate, segregate, suspend and store fulvic acid and humic acid from the at least one humate source includes a process for automatically sampling and detecting dissolved salts in the mixture using a vacuum coupled pipet and saline sensors and analyzing the sample using a chemical analyzer to determine a total dissolved salts concentration in the mixture and using a desalinating reverse osmosis device for reducing the total dissolved salts concentration in the mixture below 200 ppm. Processing the chopped and pulverized at least one humate source and the processed water product mixture to separate, segregate, suspend and store fulvic acid and humic acid from the at least one humate source includes a process for automatically sampling and detecting chlorine in the mixture using a vacuum coupled pipet and chlorine sensors and analyzing the sample using a chemical analyzer to determine a chlorine concentration in the mixture and using an Ultra Violet light device for removing the chlorine concentration in the mixture.

Processing the chopped and pulverized at least one humate source and the processed water product mixture to separate, segregate, suspend and store fulvic acid and humic acid from the at least one humate source includes a process for automatically sampling and detecting microorganisms in the mixture using a vacuum coupled pipet and biological sensors and using an Ultra Violet light device for killing the microorganisms in the mixture. Processing the chopped and pulverized at least one humate source and the processed water product mixture for separating, segregating, suspending and storing fulvic acid and humic acid from the at least one humate source includes a process for adsorbing humic acid molecules on activated carbon and separating and segregating fulvic acid molecules from the mixture and conveying a concentration of separated fulvic acid molecules into a fulvic acid molecules storage tank.

Processing the chopped and pulverized at least one humate source and the processed water product mixture to separate, segregate, suspend and store fulvic acid and humic acid from the at least one humate source includes a process for desorbing humic acid molecules from activated carbon attachment and separating and segregating humic acid molecules from the mixture and conveying a concentration of separated humic acid molecules into a humic acid molecules storage tank. Creating at least one or more beverage product including water beverage, flavored beverages, alcoholic beverages, and supplements and food additives for human consumption using the separated, segregated, suspended and stored fulvic acid, humic acids and other ingredients including vitamins including vitamin B6 and B12. Creating at least one or more beverage product including water beverage, flavored beverages, alcoholic beverages, and supplements and food additives for human consumption using the separated, segregated, suspended and stored fulvic acid, humic acids and other ingredients including vitamins and including flavorings and additives including spicy black cherry flavoring, apple grape flavoring, peach mango flavoring, citrus mint flavoring, coffee berry extract, L-theanine, ginseng, caffeine, guarana, sage, basil, citicoline (or CDP-choline), and other flavorings and additives.

Another embodiment includes an apparatus including a device for treating at least one water source including chlorinated municipal water, flowing unchlorinated well water, stream/spring water, and ocean water for producing a potable water product including oxygenated water and distilled water including adjusting pH level .gtoreq.8.5 and <10; a device for chopping and pulverizing at least one humate source including humus soil, coal, ocean water, inland stream water, and degradated plants; a device for mixing the chopped and pulverized at least one humate source with the processed water product; a device for humic-fulvic acid separation including a humic-fulvic acid separation chamber for separating, segregating, suspending and storing humic acid and fulvic acid molecules from at least one humate source and adjusting pH level .gtoreq. 8.5 and <10; and a device for mixing and processing ingredients including humic acid, fulvic acid, vitamins and flavorings and additives for creating products for human consumption including water beverages, flavored beverages, alcoholic beverages, and supplements and food additives.

The device for treating at least one water source for producing a potable water product includes modules for filtering suspended particulates, disposing of particulate waste, detecting salinity concentration, desalinating using reverse osmosis devices, detecting chlorine concentration, dechlorinating using ultra-violet devices, detecting fluoride, defluoridating using ultra-violet light devices and activated carbon adsorption devices, sterilizing using ultra-violet, oxygenating water using electrolysis, distilling water, detecting pH level and adjusting pH level using base injection to a pH level .gtoreq.8.5 and <10. The device for humic-fulvic acid separation includes a humic-fulvic acid separation chamber using activated carbon for adsorption of humic acid molecules, for separating, segregating, suspending and storing humic acid and fulvic acid molecules from at least one humate source and adjusting pH level .gtoreq.8.5 and <10. The humic-fulvic acid separation chamber includes burners for raising a mixture temperature and a pH control device for adjusting a pH level .gtoreq. 8.5 and <10. The device for mixing and processing ingredients including treated potable water, humic acid, fulvic acid, vitamins and flavorings and additives for creating products for human consumption includes vitamins B6 and B12, flavorings and additives including spicy black cherry flavoring, apple grape flavoring, peach mango flavoring, citrus mint flavoring, coffee berry extract, L-theanine, ginseng, caffeine, guarana, sage, basil, citicoline (or CDP-choline), and other flavorings and additives.

In yet another embodiment an apparatus includes a water treatment module for processing at least one water source including chlorinated municipal water, unchlorinated well water, stream/spring water, and ocean water for producing a potable water including oxygenated water and distilled water; a humate source treatment module for processing at least one humate source including humus soil, coal, ocean water, inland stream water, and degradated plants for extracting humic acid and fulvic acid from a mixture of treated potable water and at least one humate source for human consumption; and a human consumption product processing module for mixing and combining treated potable water, humic acid, fulvic acid, vitamins and flavorings and additives for creating products for human consumption including water beverages, flavored beverages, alcoholic beverages, and supplements and food additives.

The water treatment module includes processes for filtering suspended particulates, disposing of particulate waste, detecting salinity concentration, desalinating using reverse osmosis devices, detecting chlorine concentration, dechlorinating using ultra-violet devices, detecting fluoride, defluoridating using ultra-violet light devices and activated carbon adsorption devices, sterilizing using ultra-violet, detecting pH level and adjusting pH level using base injection to a pH level .gtoreq.8.5 and <10. The humate source treatment module includes processes for chopping and pulverizing at least one humate source, and mixing the chopped and pulverized at least one humate source with the processed water product. The humate source treatment module includes processes for separating, segregating, suspending and storing fulvic acid and humic acid from the at least one humate source. The human consumption product processing module includes processes for mixing and combining some or all ingredients including treated potable water, humic acid, fulvic acid, vitamins and flavorings and additives for creating products for human consumption includes vitamins B6 and B12, flavorings and additives including spicy black cherry flavoring, apple grape flavoring, peach mango flavoring, citrus mint flavoring, coffee berry extract, L-theanine, ginseng, caffeine, guarana, sage, basil, citicoline (or CDP-choline), and other flavorings and additives and adjusting the ingredient mixtures to a pH level .gtoreq.8.5 and <10.

Computer Controlled Monitoring and Processes

In another embodiment, the invention includes computer controlled monitoring and processes for creating the above-mentioned beverages for human consumption. For example, during each process, sensors and tracking devices can be connected to each device that processes, mixes, sterilizes, etc. the beverage to ensure the beginning, intermediate and final processes are controlled to allow the final product to be suitable and meet all safety and regulatory standards for human consumption. In addition, RFID, Bluetooth, NFC, etc., sensors and devices can be coupled to the final bottled beverage product to track the beverage and/or to track the quality and consumption of the beverage. A mobile device application can be wirelessly coupled to the sensors and devices to allow a user to remotely and incessantly monitor and observe the consumption, quality and quantity of the beverage and/or the ingredients.

The foregoing has described the principles, embodiments and modes of operation of the embodiments. However, the embodiments should not be construed as being limited to the particular embodiments discussed. The above described embodiments should be regarded as illustrative rather than restrictive, and it should be appreciated that variations may be made in those embodiments by workers skilled in the art without departing from the scope of the present invention as defined by the following claims.

What is claimed is:

1. A black colored beverage, comprising:
purified water safe for human consumption;
humic acid and fulvic acid suspended within the purified water, wherein the suspended humic acid and fulvic acid are present in a concentration sufficient to imbue the purified water with a black color; and
an alcoholic beverage ingredient mixed in the purified water with the suspended humic acid and fulvic acid.

2. The black colored beverage of claim 1, further comprising at least one vitamin additive mixed in the purified water.

3. The black colored beverage of claim 2, further comprising at least one of an herbal flavoring, a tea flavoring or a coffee flavoring mixed in the purified water to adjust taste of the beverage.

4. The black colored beverage of claim 1, further comprising at least one natural fruit flavoring mixed in the purified water with the suspended humic acid and fulvic acid.

5. The black colored beverage of claim 1, further comprising a soda ash solution additive mixed in the purified water to adjust a pH level of the beverage.

6. The black colored beverage of claim 1, further comprising at least one vitamin mixed in the purified water, wherein the at least one vitamin includes at least one of vitamin A, vitamin B complex, vitamin B6, vitamin B12, vitamin C, vitamin D, vitamin E, or vitamin K.

7. The black colored beverage of claim 1, further comprising at least one additive mixed in the purified water, wherein the at least one additive comprises at least one of a dietary supplement, ginseng, caffeine, an antioxidant, or an aloe extract ingredient.

8. A black colored beverage, comprising:
purified water safe for human consumption, wherein the humic acid and fulvic acid are suspended within the purified water, wherein the suspended humic acid and fulvic acid are present in a concentration sufficient to imbue the purified water with a black color;
at least one nutritional additive mixed in the purified water having the suspended humic acid and fulvic acid, wherein the at least one additive comprises at least one of a vitamin, a dietary supplement, a mineral, or a pH adjusting solution to add nutritional value:
at least one natural fruit flavoring mixed in the purified water with the suspended humic acid and fulvic acid and the at least one nutritional additive; and
an alcoholic beverage ingredient mixed in the at least one natural fruit flavoring, purified water with the suspended humic acid and fulvic acid.

9. The black colored beverage of claim 8, further comprising a carbonation ingredient mixed in the at least one natural fruit flavoring mixed in the purified water with the suspended humic acid and fulvic acid mixture.

10. The black colored beverage of claim 8, wherein the at least one nutritional additive includes a soda ash solution.

11. The black colored beverage of claim 8, further comprising at least one of an herbal flavoring, a tea flavoring, or a coffee flavoring to add taste to the beverage.

12. The black colored beverage of claim 8, wherein the at least one nutritional additive mixed in the purified water comprises at least one of vitamin A, vitamin B complex, vitamin B6, vitamin B12, vitamin C, vitamin D, vitamin E, or vitamin K to add nutritional value.

13. The black colored beverage of claim 8, wherein the at least one nutritional additive comprises at least one mineral mixed in the purified water, at least one trace element or an electrolyte.

14. The black colored beverage of claim 8, further comprising caffeine mixed in the purified water and wherein the at least one additive comprises vitamin C mixed in the purified water.

* * * * *